US006656499B1

(12) United States Patent
Foldvari et al.

(10) Patent No.: US 6,656,499 B1
(45) Date of Patent: Dec. 2, 2003

(54) COMPOSITION FOR TRANSDERMAL AND DERMAL ADMINISTRATION OF INTERFERON-α

(75) Inventors: Marianna Foldvari, Saskatoon (CA); Sam Attah-Poku, Saskatchewan (CA)

(73) Assignee: PharmaDerm Laboratories, Ltd. (CA)

( * ) Notice: Subject to any disclaimer, the term of this patent is extended or adjusted under 35 U.S.C. 154(b) by 0 days.

(21) Appl. No.: 09/709,691

(22) Filed: Nov. 10, 2000

Related U.S. Application Data

(60) Provisional application No. 60/165,107, filed on Nov. 12, 1999, and provisional application No. 60/195,549, filed on Apr. 7, 2000.

(51) Int. Cl.[7] ......................... A61K 9/127; A61K 31/70

(52) U.S. Cl. ............................................ 424/450; 514/4

(58) Field of Search ............................ 424/450; 514/54

(56) References Cited

U.S. PATENT DOCUMENTS 4,929,442 A 5/1990 Powell
5,853,755 A 12/1998 Foldvari
5,993,852 A * 11/1999 Foldvari et al. ............ 424/450
6,002,961 A 12/1999 Mitragotri et al.

FOREIGN PATENT DOCUMENTS

WO WO 96/11705 4/1996

OTHER PUBLICATIONS

Santus and Baker, "Transdermal enhancer patent literature", Journal of Controlled Release, 25 (1993).*

Foldvari et al. "Dermal and transdermal delivery of protein pharmaceuticals lipid–based delivery systems for interferon–alpha" Biotechnol. Appl. Biochem 30, 129–137 (1999).* du Plessis, J., et al., "Research Articles Topical delivery of liposomally encapsulated gamma–interferon" *Antiviral Research 18*:259–265 (1992).

Foldvari, M., et al., "Dermal and transdermal delivery of protein pharmaceuticals: lipid–based delivery systems for interferon α" *Biotechnol. Appl. Biochem. 30*:129–137 (1999).

Ogiso, T., et al., "Mechanism for Enhancement Effect of Lipid Disperse System on Percutaneous Absorption" *Journal of Pharmaceutical Sciences 85*(1):57–64 (1996).

Weiner, N., et al., "Topical Delivery of Liposomally Encapsulated Interferon Evaluated in a Cutaneous Herpes Guinea Pig Model" *Antimicrobial Agents and Chemotherapy 33*(8):1217–1221 (1989).

* cited by examiner

*Primary Examiner*—Jose' G. Dees
*Assistant Examiner*—Robert M DeWitty
(74) *Attorney, Agent, or Firm*—Judy M. Mohr; Perkins Coie LLP

(57) ABSTRACT

A composition for transdermal and dermal administration of interferon-α is described. The composition is comprised of lipid vesicles including a fatty acylated amino acid and an oil-in-water emulsion. Interferon-α is entrapped in the vesicles.

46 Claims, 5 Drawing Sheets

COMPOSITION FOR TRANSDERMAL AND DERMAL ADMINISTRATION OF INTERFERON-α

This application claims the benefit of U.S. Provisional Application No. 60/165,107, filed Nov. 12, 1999 and of U.S. Provisional Application No. 60/195,549 filed Apr. 7, 2000, both of which are incorporated herein by reference in their entirety.

FIELD OF THE INVENTION

The present invention relates generally to the area of drug delivery, and more particularly to the area of dermal and transdermal drug delivery of interferon-α.

BACKGROUND OF THE INVENTION

Interferons (IFNs) are a well known family of cytokines secreted by a large variety of eukaryotic cells upon exposure to various mitogens. The interferons have been classified by their chemical and biological characteristics into three groups: IFN-α (leukocytes), IFN-beta (fibroblasts), and IFN-gamma (lymphocytes). IFN-alpha and beta are known as Type I interferons; IFN-gamma is known as Type II or immune interferon. The IFNs exhibit anti-viral, immunoregulatory, and antiproliferative activity.

Interferons are produced and secreted by most nucleated cells in response to viral infection as well as other antigenic stimuli. Interferons render cells resistant to viral infection and exhibit a wide variety of actions on cells. They exert their cellular activities by binding to specific membrane receptors on the cell surface. Once bound to the cell membrane, interferons initiate a complex sequence of intracellular events, including the induction of certain enzymes, suppression of cell proliferation, immunomodulating activities such as enhancement of the phagocytic activity of macrophages and augmentation of the specific cytotoxicity of lymphocytes for target cells, and inhibition of virus replication in virus-infected cells.

Oral, nasal, transdermal and even buccal and rectal routes are being investigated as potentially feasible routes to administer protein drugs, such as interferons. However, administration of polypeptides poses particular concerns. For example, the site, or route, of administration is frequently hostile to the polypeptide, e.g., orally delivered proteins are subjected to harsh conditions prior to absorption through the gastro-intestinal tract. Similarly, during absorption through the nasal mucosa considerable metabolism may occur. Another problem is that poor absorption of sufficient amounts of drug through respective barrier layers at the site of administration may be a significant factor in failure to achieve a pharmacological response.

Of these alternative routes of administration, transdermal drug delivery offers several advantages over that more traditional delivery methods, such as injections and oral delivery. Compared to oral delivery, transdermal delivery avoids gastrointestinal drug metabolism, reduces the first pass effect, and can provide a sustained release of the drug. Compared to injections, transdermal delivery eliminates the associated pain and the possibility of infection.

Theoretically, the transdermal route of drug administration could be advantageous in the delivery of many therapeutic polypeptides and proteins because these compounds are susceptible to gastrointestinal degradation and exhibit poor gastrointestinal uptake. Some proteins are cleared rapidly from the blood and need to be delivered at a sustained rate in order to maintain their blood concentration at a therapeutic level.

While transdermal delivery offers an advantageous alternative to oral delivery and injections, its applications are restricted to only a few drugs because of the extremely low skin permeability to drugs. A variety of approaches have been disclosed for enhancing transdermal uptake of drugs. These include the use of chemicals to either modify the structure of the skin or to increase the drug concentration in a transdermal device, application of electric fields to create transient transport pathways (electroporation) or to increase the mobility of charged drugs through the skin (inotophoresis), and application of ultrasound (sonophoresis).

SUMMARY OF THE INVENTION

Accordingly, it is an object of the invention to provide a composition for administration of an interferon polypeptide, transdermally.

It is a specific object of the invention to provide a composition for transdermal administration of interferon-α that delivers a sufficient amount of the drug for treatment of a condition that response to interferon-α.

In one aspect, the invention includes an interferon-α composition comprising biphasic lipid vesicles comprised of (i) a lipid bilayer comprising a phospholipid and a fatty acylated amino acid; (ii) an oil-in-water emulsion entrapped in the biphasic lipid vesicles, where the oil-in-water emulsion is stabilized by a surfactant; and (iii) interferon-α entrapped in the vesicles. The composition when applied to the skin of a subject is effective to administer a therapeutically effective amount of interferon-α.

In one embodiment, the acylated amino acid is represented by the formula:

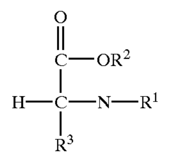

wherein $R^1$ is an acyl group having from 1–20 carbons, $R^2$ is hydrogen or an alkyl group, and $R^3$ corresponds to a modified or unmodified R group of a selected amino acid.

The acylated amino acid, in one embodiment, is selected to achieve dermal administration of interferon-α for treatment of a local, topical condition.

In another embodiment, the acylated amino acid is effective to achieve transdermal administration of interferon-α.

In a preferred embodiment, $R^2$ in the acylated amino acid is $((CO)C_{19}H_{39})$. In particular, when $R^2$ is $((CO)C_{19}H_{39})$ the amino acid is serine or threonine. Another preferred acylated amino acid is monolauroyl lysine.

In still another embodiment, the oil-in-water emulsion in the biphasic lipid vesicles further comprises a fatty alcohol. For example, the fatty alcohol can have between about 8–24 carbon atoms. In another embodiment, the oil-in-water emulsion further comprises a triglyceride, such as pharmaceutically-acceptable oil, such as canola oil and olive oil.

In yet another embodiment, the oil-in-water emulsion is further comprised of a fatty glyceride dispersed in the water phase and stabilized by the surfactant. Such a fatty glyceride can be, for example, glycerol monostearate.

The lipid bilayer of the vesicles can further comprise of a sterol.

In another aspect, the invention includes a composition for administration of interferon-α, comprising biphasic lipid vesicles comprised of (i) a lipid bilayer comprised of a phospholipid and an amino acid acylated; (ii) an oil-in-water emulsion entrapped in the biphasic lipid vesicles, where the oil-in-water emulsion is comprised of a triglyceride that is dispersed in a water phase containing a fatty alcohol and that is stabilized by a surfactant; and (iii) interferon-α entrapped in the vesicles. The composition when applied to the skin of a subject is effective to administer a therapeutically effective amount of interferon-α.

In still another aspect, the invention includes a method of administering a therapeutically effective amount of interferon-α to a subject, comprising preparing biphasic lipid vesicles as described above. The biphasic lipid vesicles are then contacted with the skin of a subject for transdermal or dermal delivery, depending on the selected acylated amino acid.

In a further aspect, the invention includes a method of treating human papilloma virus in a subject. The method includes preparing biphasic lipid vesicles as described above and contacting the biphasic lipid vesicles with the skin of a subject, or more preferably, applying the lipid vesicles to the site of the infection.

These and other objects and features of the invention will be more fully appreciated when the following detailed description of the invention is read in conjunction with the accompanying drawings.

DETAILED DESCRIPTION OF THE INVENTION

I. DEFINITIONS

Figure 1A:
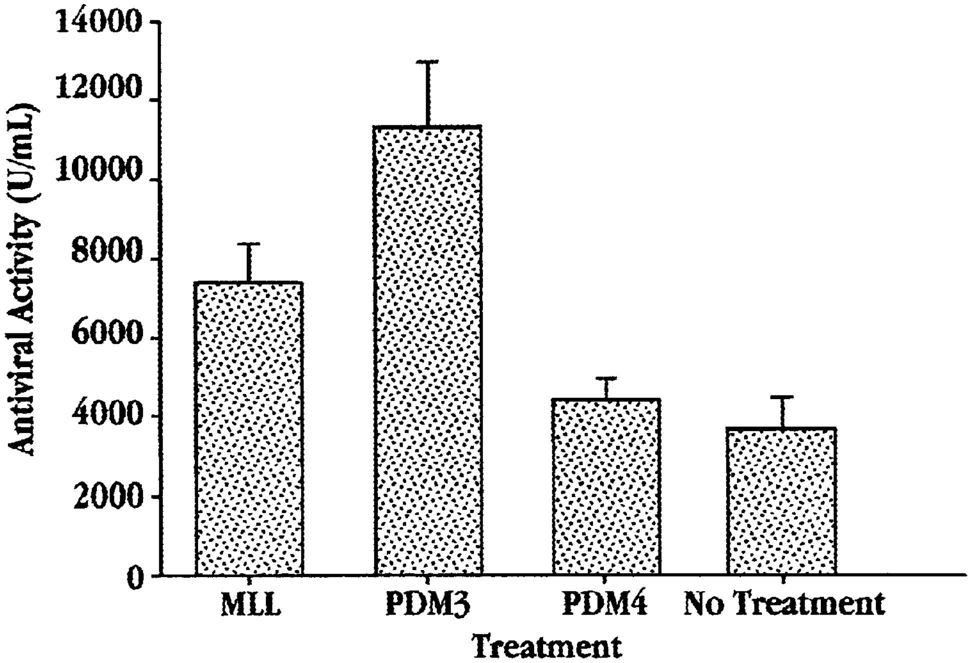
FIG. 1A is a bar graph showing the antiviral activity in serum taken from guinea pigs after transdermal administration of IFN-α from biphasic lipid vesicles containing IFN-α and monolauroyl lysine (MLL), N-eicosanoyl-L-serine (PDM3) or N-eicosanoyl threonine (PDM4) entrapped in the lipid vesicles.

"Transdermal" as used herein intends transport of an agent across the stratum corneum for introduction into systemic circulation.

"Dermal" as used herein intends transport of an agent across the stratum corneum and into the viable epidermis for treatment of a topical skin disorder that responds to local, non-systemic administration of an agent. It will be appreciated that some of the agent intended for dermal therapy may be transdermally administered, however typically not in an amount sufficient for therapy.

"Therapeutically effective amount" intends an amount of interferon-α sufficient to reduce the symptoms associated with a disease or condition and/or lessen the severity of the disease or condition. The condition can be a topical, local condition, such as genital warts, or a more pervasive condition, such as a viral infection. A therapeutically effective amount is understood to be in context to the condition being treated, where the actual effective amount is readily discerned by those of skill in the art.

"Amino acid" refers to any carboxylic acid having at least one free amine group, including naturally-occurring and synthetic amino acids.

"Acylated amino acid" refers to an amino acid modified at one or more amine groups with an acylating agent that reacts with an amine group.

"Fatty-acylated amino acid" refers to an acylated amino acid where the acyl group has more than about 8 carbon atoms.

An "R group of an amino acid" as used herein refers to the R group in the general structure [(COOH)CHNH$_2$(R)], where R represents the moiety that individualizes each amino acid. R is selected from H (glycine), $CH_3$ (alanine), $CH_2OH$ (serine) $CH_2COOH$ (aspartic acid), $(CH_2)_3NHC(NH)NH_2$ (arginine), $CH(CH_3)_2$ (valine), $CHOH(CH_3)$ (threonine), $CH_2CH_2COOH$ (glutamic acid), $CH_2CH(CH_3)_2$ (leucine), $CH_2SH$ (cysteine), $CH_2(C(NH)(CH)(N)(CH))$ (histidine), $(CH_2)_4NH_2$ (lysine), $CH(CH_3)CH_2CH_3$ (isoleucine), $CH_2(C_6H_4)OH$ (tyrosine), $CH_2(CONH_2)$ (asparagine), $(CH_2)_2SCH_3$ (methionine), $(CH_2)_3$ (proline), $CH_2C_8NH_6$ (tryptophan), $CH_2(C_6H_5)$ (phenylalanine) and $(CH_2)_2(C)(O)(NH_2)$ (glutamine).

"Interferon-α" is abbreviated herein as "IFN-α" and intends all of the known and unknown subtypes including but not limited to IFN-$\alpha_1$, IFN-$\alpha_2$, IFN-$\alpha_4$, IFN-$\alpha_5$, IFN-$\alpha_8$, IFN-$\alpha_7$, IFN-$\alpha_{10}$, IFN-$\alpha_{14}$, IFN-$\alpha_{17}$, IFN-$\alpha_{21}$, and their variants including but not limited to IFN-$\alpha_{1a}$, IFN-$\alpha_{2a}$, IFN-$\alpha_{2b}$, IFN-$\alpha_{2c}$, IFN-$\alpha_{4a}$, IFN-$\alpha_{4b}$, IFN-$\alpha_{7a}$, IFN-$\alpha_{7b}$, IFN-$\alpha_{7c}$, IFN-$\alpha_{8b}$, IFN-$\alpha_{10a}$, IFN-$\alpha_{14a}$, IFN-$\alpha_{14b}$, IFN-$\alpha_{14c}$, IFN-$\alpha_{17b}$, IFN-$\alpha_{21a}$, IFN-$\alpha_{21b}$.

II. TRANSDERMAL BIPHASIC LIPID VESICLE COMPOSITION

The present invention provides a composition for transdermal administration IFN-α. The composition is comprised of biphasic lipid vesicles, typically in suspension form, for application to the skin of a subject afflicted with a condition treatable with IFN-α. Entrapped in the vesicles is an acylated amino acid which, as will be demonstrated, is effective to significantly enhance the transport of IFN-α across the skin for systemic and/or local therapy. In this section, the composition and preparation of biphasic lipid vesicles and of the acylated amino acids will be described.

1. Biphasic Lipid Vesicles

The lipid vesicles of the present invention are comprised of a lipid component for formation of lipid bilayers. An oil-in-water emulsion, which is described below, is incorporated into the central core compartment of the vesicles and between the lipid bilayers. These vesicles are referred to herein as "biphasic lipid vesicles". The term "lipid vesicle" used herein intends biphasic lipid vesicles. Biphasic lipid vesicles have been described, for example, in PCT Publication Nos. WO 95/03787, WO 99/11247 and in U.S. Pat. No. 5,853,755, which are herein incorporated by reference in their entirety.

A. Lipid Component

Biphasic lipid vesicles in accordance with the present invention are prepared from a selected lipid composition comprised of one or more lipids. The composition will include at least one vesicle-forming lipid, by which is meant a lipid that upon hydration with an aqueous medium spontaneously forms lipid bilayers, where the polar head group of the lipid is oriented for contact with the aqueous medium. The vesicle-forming lipids have one or two hydrocarbon tails, typically an acyl chain. There are a variety of synthetic vesicle-forming lipids and naturally-occurring vesicle-forming lipids suitable for use, such as the phospholipids, which include phosphatidylcholine, phosphatidylethanolamine, phosphatidylserine, phosphatidylinositol, phosphatidic acid, and a preferred lipid is fully hydrogenated soybean phosphatidylcholine. These lipids have two hydrocarbon chains typically between about 14–22 carbon atoms in length, and can have varying degrees of unsaturation. The lipids can be obtained commercially or prepared according to published methods.

In addition to the vesicle-forming lipid component, the biphasic lipid vesicles of the present invention can further include other lipid components capable of being stably incorporated into lipid bilayers. For example, glycolipids, ceramides and sterols, such as cholesterol, coprostanol, cholestanol and cholestane, long chain fatty acids ($C_{16}$ to $C_{22}$), such as stearic acid, can be incorporated into the lipid bilayer. Other lipid components that may be used include fatty amines, fatty acylated proteins, fatty acylated peptides, oils, fatty alcohols, glyceride esters, petrolatum and waxes. As will be described below, a skin permeation enhancer in the form of an acylated amino acid can also be included in the lipid vesicle lipid components.

Typically, the liposomes include between about 1–40% of vesicle-forming lipid, more preferably from about 5–25% (percentages are weight percentages based on the total liposome composition, including the oil-in-water emulsion phase described below). The hydrophilic solvent other than water typically constitutes between 1–15% of the liposome, and the acylated amino acid constitutes between 0.1–5%. Cholesterol, or other sterol, when added, is typically in the 1–10% range.

B. Oil-In-Water Emulsion

As noted above, the biphasic lipid vesicles include an oil-in-water emulsion entrapped in the vesicles' aqueous spaces. The oil-in-water emulsion is comprised of water, a selected lipophilic, hydrophobic component, and a surfactant. The oil-in-water emulsion is one having water as the continuous phase and the lipophilic component as the dispersed phase. The surfactant serves to stabilize the emulsion, and, during formation of the emulsion, it is added to either the water phase or the lipophilic, oil phase, depending on the hydrophilic-lipophilic balance (HLB) of the surfactant. Typically, the surfactant is mixed with the water and this mixture is added to the oily lipohpilic phase for homogenization and formation of the emulsion.

In a preferred embodiment, the stabilizing surfactant is other than a vesicle-forming lipid, e.g., the surfactant is one which does not spontaneously form lipid bilayers. The oil-in-water emulsion is stable by virtue of the oil droplets in the dispersed phase being surrounded by the surfactant. That is, the hydrophilic portion of each surfactant molecule extends into the aqueous phase of the emulsion and the hydrophobic portion is in contact with the lipophilic droplet. If the emulsion is not surfactant-stabilized prior to contact with the vesicle-forming lipids, the vesicle-forming lipids may act to first stabilize the emulsion rather than form lipid bilayers around the oil-in-water emulsion.

Surfactants suitable for formation of the oil-in-water emulsion are numerous, including both cationic, anionic and nonionic or amphoteric surfactants. In one embodiment, the preferred surfactant is a cationic surfactant, such as linoleamidopropyl propylene glycol-dimonium chloride phosphate, cocamidopropyl propylene glycol-dimonium chloride phosphate and stearamido propylene glycol-dimonium chloride phosphate. These are synthetic phospholipid complexes commercially available from DEBRO (Mississauga, Ontario, Canada) sold under the tradenames Phospholipid EFA™, Phospholipid SV™ and Phospholipid SVC™, respectively.

Exemplary anionic surfactants include acylglutamates, such as triethanolamine-cocoyl glutamate, sodium lauroyl glutamate, sodium hydrogenated tallow glutamate and sodium cocoyl glutamate.

Exemplary nonionic surfactants include naturally derived emulsifiers, such as polyethyleneglycol-60 almond glycerides, avocado oil diethanolamine, ethoxylated jojoba oil (polyethyleneglycol-40 jojoba acid and polyethyleneglycol-40 jojoba alcohol); polyoxyethylene derivatives, such as polyoxyethylene-20 sorbitan monooleate and polyoxythethylene-20 sorbitan monostearate; lanolin derivatives, such as polychol 20 (LANETH 20) and polychol 40 (LANETH 40); and neutral phosphate esters, such as polypropyleneglycol-cetyl ether phosphate and diethanolamine oleth-3 phosphate.

The oil component of the emulsion can be selected from a variety of lipophilic compounds, including natural and synthetic triglycerides, fatty glycerides, solid and semi-solid waxes and mixtures thereof. In a preferred embodiment, the primary oil component is a triglyceride selected from synthetic and natural oils, such as olive oil, canola oil, sunflower oil and other oils recited in Col. 12, lines 20–42 of U.S. Pat. No. 5,854,755, which is herein incorporated by reference. A preferred fatty glyceride is glycerol monostearate and a preferred wax is beeswax. As will be described below, biphasic lipid vesicles prepared in support of the invention included as the primary oil component a triglyceride, with a fatty glyceride and a wax added as minor components.

In one preferred embodiment, the oil-in-water emulsion further includes a fatty alcohol, $C_nH_{n+2}O$, where n is from 2–24, more preferably from 8–24. In a preferred embodiment, the fatty alcohol is cetyl alcohol ($C_{16}H_{34}O$) or stearyl alcohol ($C_{18}H_{38}O$). The fatty alcohol is typically added to the oil phase prior to homogenization.

The oil-in-water emulsion can also include other components, such as antimicrobial agents or preservatives. Typically, these agents are admixed with the aqueous phase prior to homogenization with the oil phase. Preferred agents include hydroxylated benzoate esters, such as methyl paraben, propyl paraben, 1-(3-chlorallyl)-3,4,7-triaza-1-azoniaadamantane chloride (DOWICIL, ($C_6H_{12}N_4$($CH_2CHCHCl$)Cl), butylated hydroxytoluene (BHT), and other antimicrobial agents known to those of skill in the art.

The oil-in-water emulsion is generally prepared by mixing the water and the surfactant along with any additional hydrophilic components, such as a fatty alcohol and a preservative, in a first container. The oil components, such as a triglyceride and a fatty glyceride, are mixed in a second container. The water phase is added to the oil phase for formation of the emulsion by agitation, such as by homogenization or emulsification, or by a micro-emulsion technique which does not involve agitation. The resulting emulsion preferably has water as the continuous phase and oil as the dispersed phase. The oil droplets in the dispersed oil phase preferably have sizes of less than about 1 $\mu$m, more preferably less than about 0.5 $\mu$m, in diameter. The droplet size, of course, is readily adjusted by mixing conditions, e.g., shear and time of mixing, etc.

Typically, the liposomes include between 1–20% of the surfactant, more preferably between 2–15% (percentages are weight percentages based on the total liposome composition, including the lipid phase described above). The lipophilic oil constitutes typically between 1–10% of the liposome composition. A fatty glyceride when added is typically between 0.1–5% of the composition and a fatty alcohol, when added, is typically between 0.1–5% of the composition.

C. Acylated Amino Acids

Tables 1A–1F show exemplary acylated amino acids for use as absorption promoters in the compositions of the present invention. Generally, the acylated amino acid compounds are represented by the structure X—CO—A, where X is an aliphatic hydrocarbon group, an aryl-substituted lower hydrocarbon or an aromatic hydrocarbon group, each of which may optionally be substituted, and A is an amino acid residue which may optionally be substituted. Alternatively, the acylated amino acids are represented by the general formula:

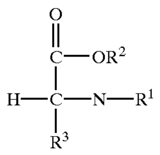

wherein $R^1$ is typically an acyl group having from 1–20 carbons, $R^2$ is hydrogen or a lower alkyl, and $R^3$ corresponds to the R group of the selected amino acid. In some cases $R^3$ includes an amino group which can be acylated, such as when $R^3$ is lysine, arginine, or glutamine, and compounds PDM5 and PDM17 in Table 1A are exemplary.

TABLE 1A
| Chemical Name | Code | Chemical Structure | Properties |
|---|---|---|---|
| N-capryloyl-L-threonine methyl ester | PDM1 | 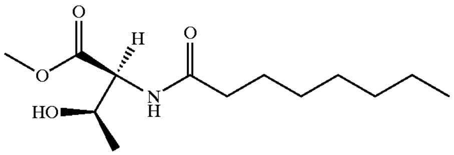 | Mwt: 259.34<br>Molecular Formula:<br>$C_{13}H_{25}NO_4$ |
| N-eicosanoyl-L-serine | PDM3 | 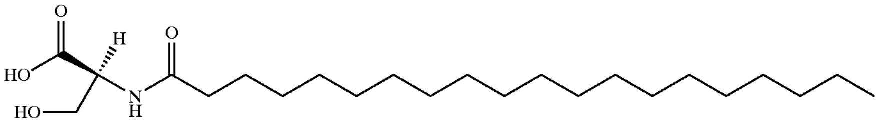 | Mwt: 399.61<br>Molecular Formula:<br>$C_{23}H_{45}NO_4$ |
| N-eicosanoyl threonine | PDM4 | 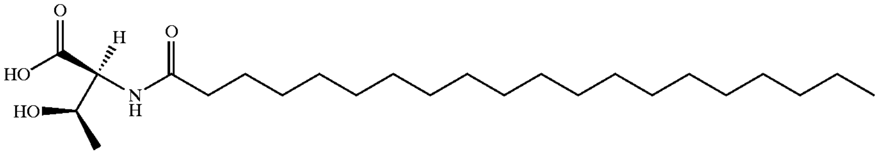 PDM-4 | Mwt: 413.62<br>Molecular Formula:<br>$C_{24}H_{47}NO_4$ |
| Nα-capryloyl-Nε-lauroyl-L-lysine methyl ester | PDM5 | 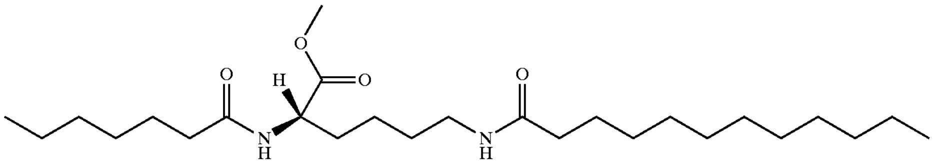 | Mwt: 468.71<br>Molecular Formula:<br>$C_{27}H_{52}N_2O_4$ |

TABLE 1A-continued
| Chemical Name | Code | Chemical Structure | Properties |
|---|---|---|---|
| Nα-palmitoyl-Nε Lauroyl-L-lysine methyl ester | PDM17 | 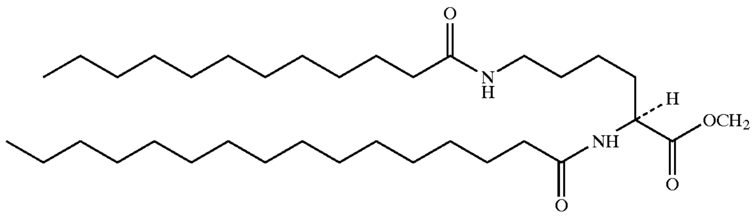 | Mwt: 580.93<br>Molecular Formula:<br>$C_{35}H_{68}N_2O_4$ |
| Nα lauroyl-Nε Lauroyl-L-lysine methyl ester | PDM18 | 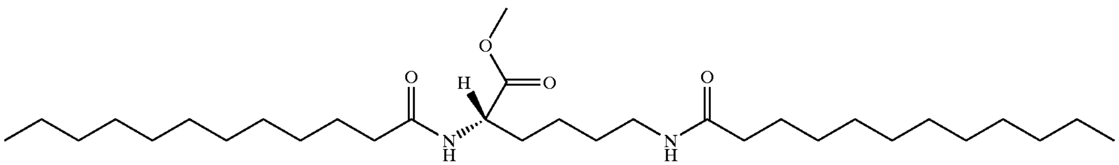 | Mwt: 524.82<br>Molecular Formula:<br>$C_{31}H_{60}N_2O_4$ |
| Nε-lauroyl-L lysine ethyl ester | PDM19 | 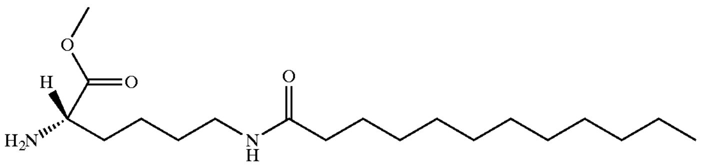 | Mwt: 356.54<br>Molecular Formula:<br>$C_{20}H_{40}N_2O_3$ |

TABLE 1B

| Chemical Name | Code | Chemical Structure | Properties |
|---|---|---|---|
| Nϵ-lauroyl-L lysine methyl ester | PDM20 | 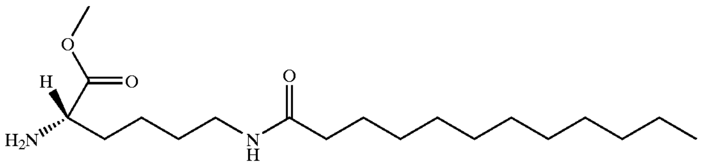 | Mwt: 342.52 Molecular Formula: $C_{19}H_{38}O_3$ |
| Nα-capryloyl-Nϵ lauroyl L-lysine ethyl ester | PDM27 | 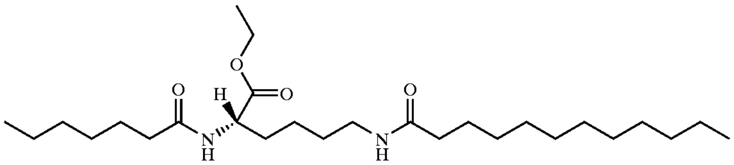 | Mwt: 482.74 Molecular Formula: $C_{28}H_{54}N_2O_4$ |
| Nα Maleoyl-Nϵ lauroyl-L-lysine ethyl ester | PDM29 | 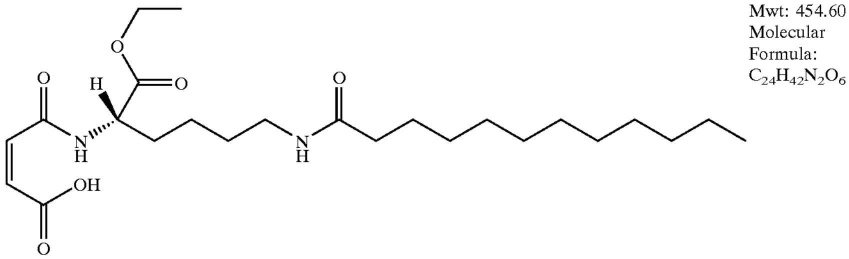 | Mwt: 454.60 Molecular Formula: $C_{24}H_{42}N_2O_6$ |
| Nϵ Lauroyl L-lysine-n-propyl ester | PDM41 | 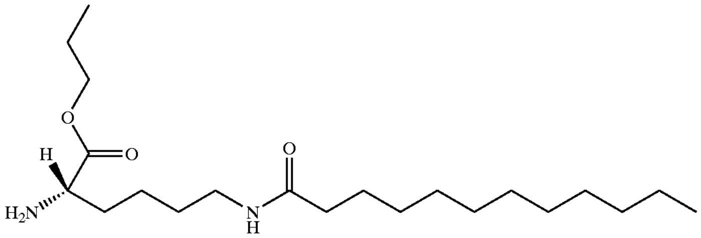 | Mwt: 370.57 Molecular Formula: $C_{21}H_{42}N_2O_3$ |
| Nϵ-Lauroyl-L-Lysine-n-butyl ester | PDM42 | 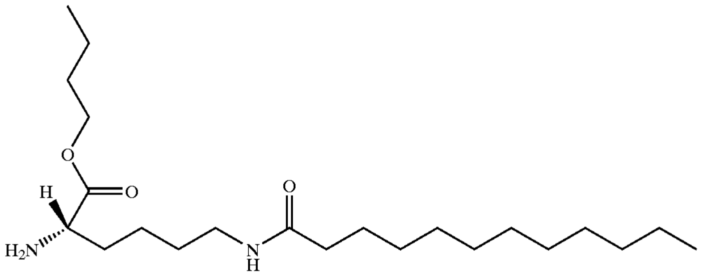 | Mwt: 384.60 Molecular Formula: $C_{22}H_{44}N_2O_3$ |
| Nϵ-Lauroyl-L-lysine-iso-amyl ester + isomer | PDM43 | 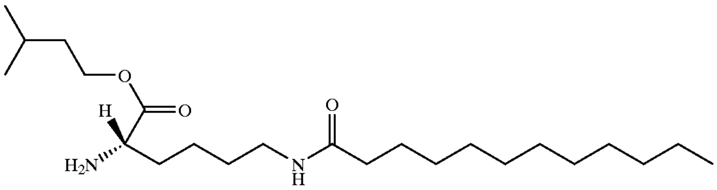 | Mwt: 398.62 Molecular Formula: $C_{23}H_{46}N_2O_3$ |

TABLE 1C

| Chemical Name | Code | Chemical Structure | Properties |
|---|---|---|---|
| Nϵ-Lauroyl-L-lysine-dodecyl ester | PDM45 | 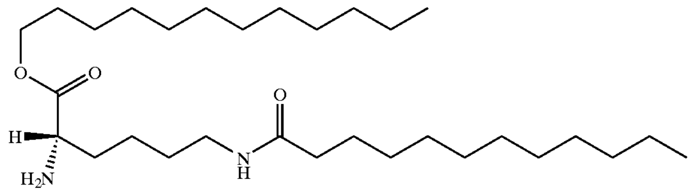 | Mwt: 496.81 Molecular Formula: $C_{30}H_{60}N_2O_3$ |
| Nα-capryloyl-N-ϵ lauroyl-L-lysine-n-propyl ester | PDM46 | 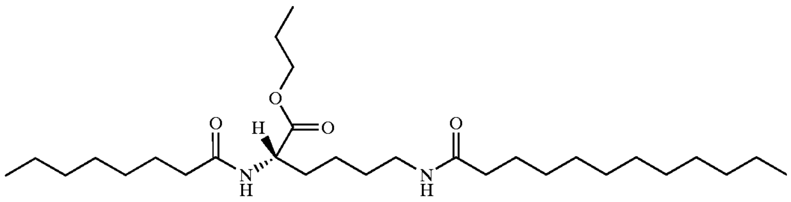 | Mwt: 496.77 Molecular Formula: $C_{29}H_{56}N_2O_4$ |
| Nα-capryloyl-N-ϵ lauroyl-L-lysine-n-butyl ester | PDM47 | 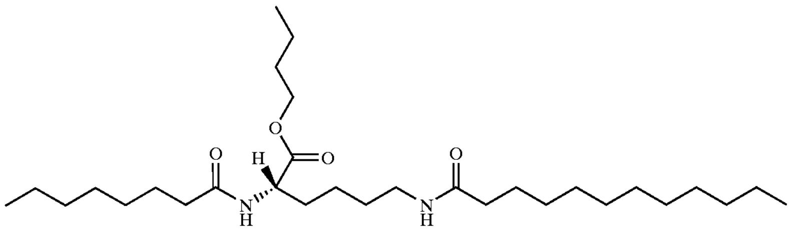 | Mwt: 510.79 Molecular Formula: $C_{30}H_{58}N_2O_4$ |
| Nα-capryloyl-Nϵ-Lauroyl-L-lysine-iso-amyl ester + isomer | PDM49 | 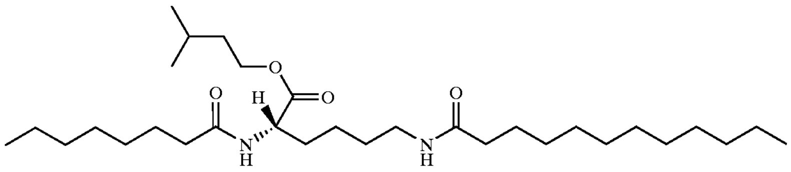 | Mwt: 524.82 Molecular Formula: $C_{31}H_{60}N_2O_4$ |
| Nα-capryloyl-N-ϵ lauroyl-L-lysine-n-dodecyl ester | PDM50 | 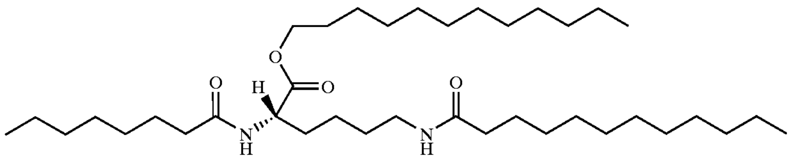 | Mwt: 623.1 Molecular Formula: $C_{38}H_{74}N_2O_4$ |
| Nα-maleoyl-Nϵ-lauroyl-L-lysine-dodecyl ester | PDM51 | 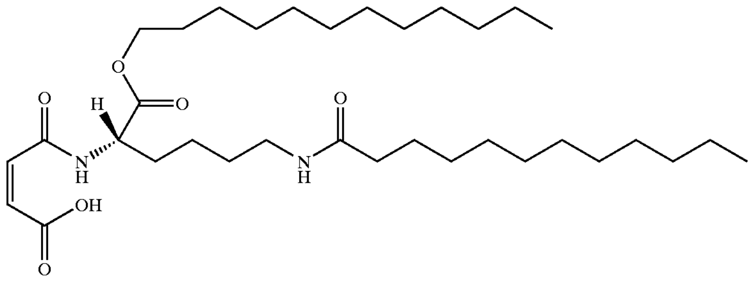 | Mwt: 594.87 Molecular Formula: $C_{34}H_{62}N_2O_6$ |

TABLE 1D

| Chemical Name | Brand Name | Code | Chemical Structure | Properties |
| --- | --- | --- | --- | --- |
| Sodium N-Stearoyl-L-Glutamate | Amisoft HS-11 (Ajinomoto USA Inc., Teaneck, NJ) | AG5 | 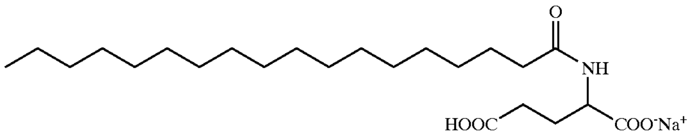 R = stearoyl | Mwt: 435.57 Molecular Formula: $C_{23}H_{42}NNaO_5$ |
| Disodium Stearoyl-L-Glutamate | Amisoft HS-21 (Ajinomoto USA Inc., Teaneck, NJ) | AG6 | 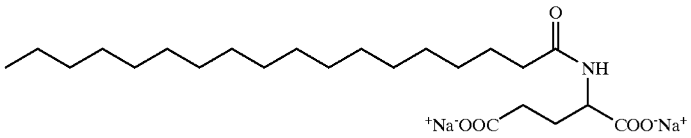 R-stearoyl | Mwt: 457.55 Molecular Formula: $C_{23}H_{41}NNa_2O_5$ |
| Sodium Lauroyl-L-Glutamate | Amisoft LS-11 (Ajinomoto USA Inc., Teaneck, NJ) | AG7 | 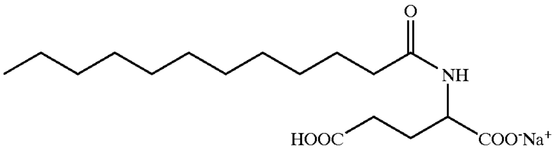 R-lauroyl | Mwt: 351.41 Molecular Formula: $C_{17}H_{30}NNaO_5$ |
| Lauroyl lysine | Amihope LL (Ajinomoto USA Inc., Teaneck, NJ) | MLL | 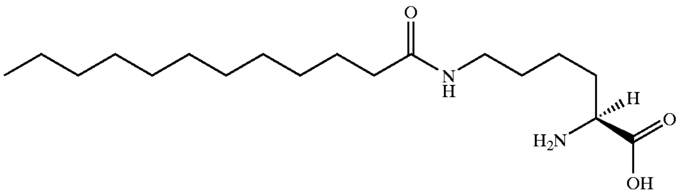 | Mwt: 328.49 Molecular Formula: $C_{18}H_{36}N_2O_3$ |
| Tea - Lauroyl Animal Collagen Amino Acids | Aminofoam C (Croda Canada, Toronto, ON) | AFC | — | Mwt: 550 |
| Tea - Lauroyl Keratin Amino Acids | Aminofoam K (Croda Canada, Toronto, ON) | AFK | — | Mwt: 550 |

TABLE 1E

| Chemical Name | Brand Name | Code | Chemical Structure | Properties |
| --- | --- | --- | --- | --- |
| Cocyl Sarcosine | Hamposyl C (Hampshire Chemical Corp., Lexington, MA) | HC | 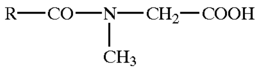 R-cocoyl | Mwt: 280. |
| Lauroyl Sarcosine | Hamposyl L (Hampshire Chemical Corp., Lexington, MA) | HL | 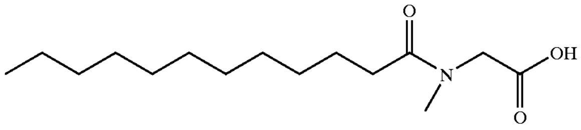 | Mwt: 271.40 Molecular Formula: $C_{15}H_{29}NO_3$ |
| Oleyl Sarcosine | Hamposyl O (Hampshire Chemical Corp., Lexington, MA) | HO | 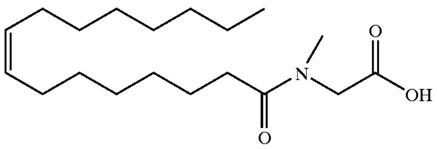 | Mwt: 325.49 Molecular Formula: $C_{19}H_{35}NO_3$ |

TABLE 1E-continued

| Chemical Name | Brand Name | Code | Chemical Structure | Properties |
|---|---|---|---|---|
| Myristoyl Sarcosine | Hamposyl M (Hampshire Chemical Corp., Lexington, MA) | HM | 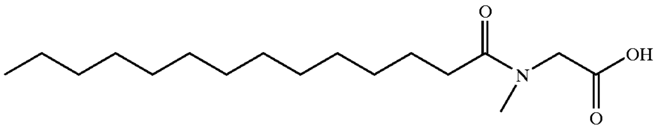 | Mwt: 299.45 Molecular Formula: $C_{17}H_{33}NO_3$ |
| N,N Dipalmitoyl Lysine | — (Canamino Inc. Ottawa, ON) | DPL | 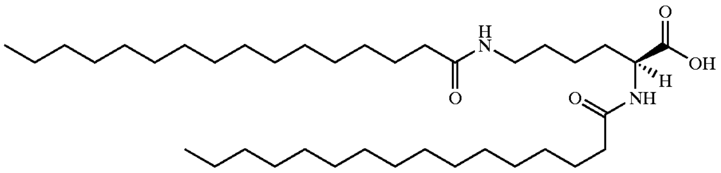 | Mwt: 623.01 Molecular Formula: $C_{38}H_{74}N_2O_4$ |
| N Cinnamoyl Phenyl alanine | — (Canamino Inc. Ottawa, ON) | CPh | 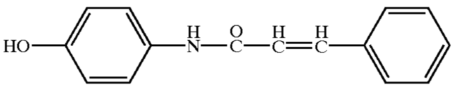 | Mwt: 239.27 Molecular Formula: $C_{15}H_{13}NO_2$ |

TABLE 1F

| Chemical Name | Brand Name | Code | Chemical Structure | Properties |
|---|---|---|---|---|
| N Myristoyl Glycine | — (Canamino Inc. Ottawa, ON) | MG | 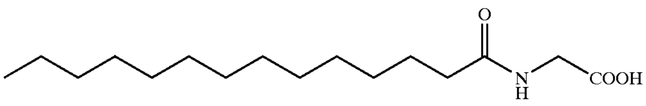 | Mwt: 285.43 Molecular Formula: $C_{16}H_{31}NO_3$ |
| N-Acetyl-L-Cysteine | — (Canamino Inc. Ottawa, ON) | AC | 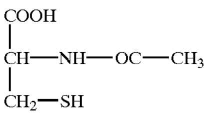 | Mwt: 239.27 Molecular Formula: $C_5H_{13}NO_2$ |
| Cocoyl Glutamate | Amisoft CA (Ajinomoto USA Inc., Teaneck, NJ) | AG1 | 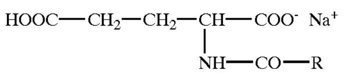 R-cocoyl | Mwt: ~400 |
| Potassium Cocoyl Glutamate | Amisoft CK11 (Ajinomoto USA Inc., Teaneck, NJ) | AG2 | 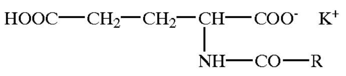 R-cocoyl | Mwt: ~400 |
| Tea Cocyl Glutamate | Amisoft CT-12 30% aqueous solution (Ajinomoto USA Inc., Teaneck, NJ) | AG3 | 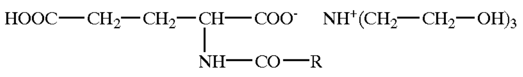 R-cocoyl | Mwt: ~400 |
| Sodium Cocoyl Glutamate & Sodium Hydrogenated Tallow-Glutamate | Amisoft GS-11 (Ajinomoto USA Inc., Teaneck, NJ) | AG4 | 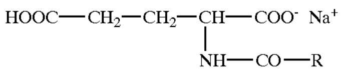 R-cocoyl-tallowyl | Mwt: 420 |

The preferred naturally occurring α-amino acids for use in the invention are alanine, arginine, asparagine, aspartic acid, cysteine, glutamic acid, glutamine, glycine, histidine, isoleucine, leucine, lysine, methionine, ornithine, phenylalanine, proline, serine, threonine, tryptophan, tyrosine, valine. Most preferred amino acids are lysine, threonine, serine, glycine, cysteine and glutamine.

Modification of α-amino acids by acylating at least one free amino group is readily performed using an acylating agent that reacts with a free amino group. The compounds listed in Tables 1A–1C were synthesized for studies conducted in support of the present invention and exemplary synthetic reaction schemes for two of the compounds, $PDM_3$ and $PDM_4$, are described in Examples 1–2. The compounds listed in Tables 1D–1F are commercially available from the vendors indicated in the second column of the tables.

D. Preparation of Biphasic Lipid Vesicles

Preparation of biphasic lipid vesicles has been described in detail, for example, in PCT Publication Nos. WO 95/03787 and in U.S. Pat. No. 5,853,755. Briefly, the selected vesicle-forming lipid and the selected acylated amino acid are solubilized in a suitable solvent, which in a preferred embodiment, is a pharmaceutically acceptable hydrophilic solvent, such as a polyol, e.g., propylene glycol, ethylene glycol, glycerol, or an alcohol, such as ethanol, or mixtures of such solvents. Depending on the physicochemical properties of the lipid components and on the selected solvent, it may be necessary to warm the mixture, for example, to between 40–80° C.

In a separate container, the surfactant-stabilized oil-in-water emulsion described above is prepared. A concentrated aqueous solution of interferon-α is also prepared, and biphasic lipid vesicles are formed by simultaneously mixing the oil-in-water emulsion and the concentrated drug solution with the solubilized lipids. The emulsion and the lipid components are mixed under conditions effective to form multilamellar vesicles having in the central compartment the oil-in-water emulsion. Example 3, discussed below, describes preparation of biphasic lipid vesicles for use in studies performed in support of the invention.

It will be appreciated that the amount of IFN-α entrapped in the lipid vesicles is readily controlled and varied by the concentration of the aqueous IFN-α solution used during lipid vesicle formation.

The size of the vesicles is typically between about 0.1–100 μm. For use in the present invention, a lipid vesicle size of between about 0.5–5 μm is preferred, which can be most readily obtained by adjusting the mixing conditions.

The composition of lipid vesicles has a consistency similar to a cream without further addition of thickening or gelling agents, and, therefore, are readily applied directly to the skin of a subject for transdermal administration of the entrapped interferon-α. Alternatively, the lipid vesicle composition can be readily incorporated into the reservoir of a transdermal device.

III. Transdermal and Dermal Delivery of Interferon-α

Biphasic lipid vesicles having entrapped IFN-α and an acylated amino acid were prepared for studies in support of the invention. These in vitro and in vivo studies will now be described.

A. In vitro

In studies performed in support of the invention, biphasic lipid vesicles were prepared as described in Example 3A. The lipid vesicles were comprised of IFN-α and an acylated amino acid selected from $PDM_1$, $PDM_3$, $PDM_4$, $PDM_5$, $PDM_{17}$, $PDM_{18}$, $PDM_{27}$ and MLL (see Tables 1A–1F for chemical name and structure). The composition of the biphasic lipid vesicles is set forth in Table 2.

TABLE 2

Biphasic lipid vesicle composition for *in vitro* study

| LIPID PHASE Component (amount)[1] | OIL-IN-WATER EMULSION Water Phase Component (amount) | Oil Phase Component (amount) |
|---|---|---|
| Phosphatidylcholine (5%) | Phospholipid EFA[2] (4%) | Olive oil (10%) |
| Acylated amino acid[3] (2%) | Methyl paraben (0.15%) | Glycerol monostearate (1%) |
| Propylene glycol (7%) | Propyl paraben (0.05%) | Synthetic beeswax (0.28%) |
| Cholesterol (2%) | Cetyl alcohol (0.6%) | |
| Stearic acid (1%) | | |

[1]amount reported as total weight percent
[2]linoleamidopropyl propylene glycol-dimonium chloride
[3]vesicles were prepared using the following acylated amino acids: PDM1, PDM3, PDM4, PDM5, PDM17, PDM18, PDM27 and MLL The vesicles were prepared by simultaneously mixing the oil-in-water emulsion and an aqueous solution containing five million units of IFN-α with the solubilized lipid phase.

After vesicle preparation, a thin layer of the lipid vesicle suspension was observed under an optical microscope (Reichert Microstar IV) to measure the vesicle particle size and size homogeneity.

As a comparative control, a propylene glycol-based formulation was prepared by dissolving the same amounts of IFN-α and the selected acylated amino acid in propylene glycol.

The in vitro diffusion of IFN-α into human skin was determined using flow-through diffusion cells, as detailed in Example 3B. About 100 mg of each test formulation was applied on the stratum corneum side of the skin and allowed to remain for 24 hours. The amount of IFN-α that penetrated into the skin was assessed using a bioassay that measures interferon antiviral activity (see Methods section below).

Table 3 shows the average amount of IFN-α in the skin at the end of the 24 hour test period, as determined by antiviral activity, for each of the test formulations.

TABLE 3

| Acylated Amino Acid[1] | Average Amount of IFN-α in skin[2] (U/mg protein): Comparative formulation: Propylene glycol + Acylated Amino Acid | Lipid vesicles + acylated amino acid | P values[3] |
|---|---|---|---|
| PDM1 | 539 ± 197 | 290 ± 172 | >0.1 |
| PDM3 | 583 ± 347 | 2022 ± 1046 | <0.05 |
| PDM4 | 868 ± 348 | 1707 ± 538 | >0.1 |
| PDM5 | 261 ± 522 | 35 ± 24 | n.s. |
| PDM17 | 306 ± 500 | 540 ± 239 | n.s. |
| PDM18 | 136 ± 74 | 84 ± 52 | n.s. |
| PDM27 | 336 ± 155 | 92 ± 13 | n.s. |
| MLL | — | 250 ± 112 | — |

[1]see Tables 1A–1F for compound name and structure
[2]n = 4
[3]by unpaired t-test, comparison of lipid vesicle formulation and PG formulation The data in Table 3 shows that incorporation of an acylated amino acid into lipid vesicles can increase the dermal and transdermal delivery of IFN-α. The data also shows that some acylated amino acids are particularly effective for dermal delivery of IFN-α, whereas other are more effective for transdermal delivery. For example, the acylated amino acids $PDM_3$ and $PDM_4$ when incorporated into lipid vesicles achieved a significant increase in delivery of IFN-α to the skin.

B. In vivo
1. Guinea Pigs

The transdermal absorption of IFN-α from formulations containing N-eicosanoyl-L-serine (PDM$_3$), N-eicosanoyl threonine (PDM$_4$) or monolauroyl lysine (MLL) entrapped in biphasic lipid vesicles was measured using guinea pigs as an in vivo model. The in vivo tests were conducted as described in Example 4. The lipid vesicles were prepared as described in Example 3A and were placed in the reservoir of a transdermal drug delivery device, similar to those described in U.S. Pat. No. 5,718,914 (which is incorporated by reference in its entirety), except that the device contained no microporous membrane or other layer between the lipid vesicle formulation and the skin of the animal. The devices were placed on a section of shaved skin of each animal.

FIG. 1A is a bar graph showing the serum antiviral activity for animals treated with the three lipid vesicle test formulations and for control animals that where untreated. As seen, the formulation containing PDM$_3$ achieved a significant increase in transdermal skin penetration.

Figure 1B:
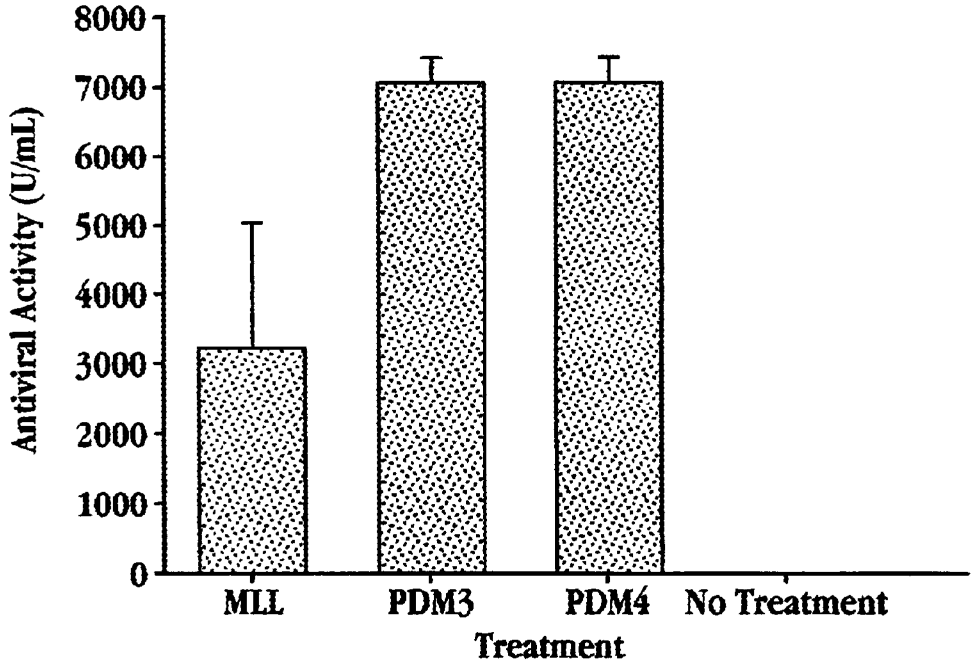
FIG. 1B is a bar graph showing the antiviral activity in skin homogenates prepared from the skin of guinea pigs after transdermal administration of IFN-α from biphasic lipid vesicles containing IFN-α and monolauroyl lysine (MLL), N-eicosanoyl-L-serine (PDM3) or N-eicosanoyl threonine (PDM4) entrapped in the lipid vesicles.

FIG. 1B is a bar graph showing the antiviral activity in skin homogenates prepared from the skin of guinea pigs after transdermal administration of the IFN-α lipid vesicle formulations. As seen, the animals treated with the lipid vesicles containing the acylated amino acids $PDM_3$ and $PDM_4$ show the highest antiviral activity at about 7,000 U/mg protein.

2. Humans

In other studies performed in support of the invention, dermal and transdermal delivery of IFN-α from biphasic lipid vesicles containing an acylated amino acid monolauroyl lysine (MLL) was evaluated. The lipid vesicles were prepared according to the process described in Example 3A with the composition set forth in Table 4.

TABLE 4

Composition of Biphasic Lipid Vesicles for Transdermal Administration of IFN-α to Human Subjects

| | OIL-IN-WATER EMULSION | |
|---|---|---|
| LIPID PHASE Component (amount)[1] | Water Phase Component (amount) | Oil Phase Component (amount) |
| Phosphatidylcholine (10%) | Phospholipid EFA[2] (4%) | Canola oil (4%) |
| monolauroyl lysine[3] (2%) | Methyl paraben (0.15%) | Glycerol monostearate (1%) |
| Propylene glycol (7%)% | Propyl paraben (0.05%) | Beeswax (0.28%) |

TABLE 4-continued

Composition of Biphasic Lipid Vesicles for Transdermal Administration of IFN-α to Human Subjects

| | OIL-IN-WATER EMULSION | |
|---|---|---|
| LIPID PHASE Component (amount)[1] | Water Phase Component (amount) | Oil Phase Component (amount) |
| Cholesterol (2%) | DOWICIL 200[4] (0.05%) Cetyl alcohol (0.6%) | |

[1]amount reported as volume percent
[2]linoleamidopropyl propylene glycol-dimonium chloride
[3]see Table 1 for chemical name and structure
[4]Dowicil = 1-(3-chlorallyl)-3,4,7-triaza-1-azoniaadamantane chloride The lipid vesicles were prepared with three dosages of IFN-α, 5 MU, 15 MU and 40 MU, by addition of an aqueous solution at the dosage concentration to the lipid phase during vesicle formation, as described in Example 5A.

The human subjects were divided randomly into three groups for treatment with a transdermal patch containing a lipid vesicle compositions at one of the three IFN-α concentrations. The experimental protocol is set forth in Example 5C. Briefly, in Phase I of the study, a placebo transdermal patch containing the biphasic lipid vesicles described in Table 4 and prepared as described in Examples 5A–5B with no IFN-α was adhered to the inner upper arm. After treatment with the placebo, skin biopsies and blood samples were collected from each subject. In Phase II of the study, each subject was treated with a transdermal patch containing IFN-α entrapped in biphasic lipid vesicles at one of the three concentrations: 5 MU/g formulation/patch, 15 MU/g formulation/patch or 40 MU/g formulation/patch. After treatment for 48 hours, skin biopsies and blood samples were taken and analyzed. The biopsy samples were analyzed by immunohistochemistry, antiviral assay, ELISA and 2-5A synthetase assays. The blood samples were used to prepare serum for the antiviral and ELISA assays and to extract peripheral blood mononuclear cells for the 2-5A synthetase assay.

3. Dermal Drug Delivery: Analysis of Skin Biopsies

Figure 2A:
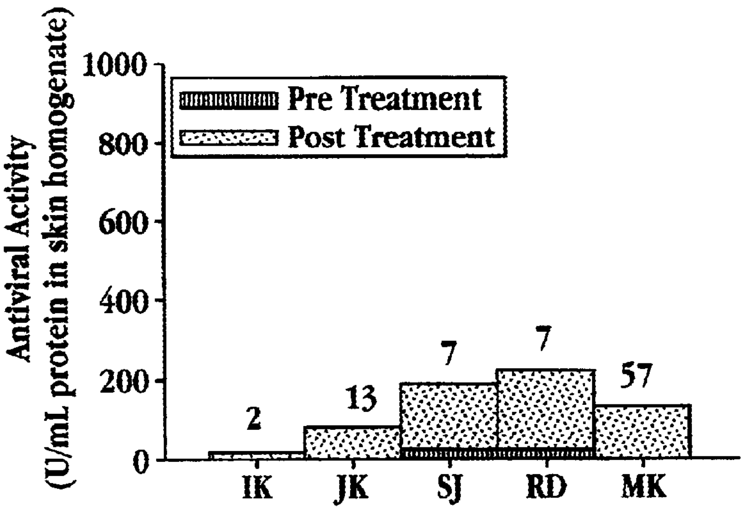
FIGS. 2A–2C are graphs showing the antiviral activity in skin biopsy samples taken from human subjects after transdermal administration of IFN-α from biphasic lipid vesicles containing monolauroyl lysine and IFN-α at dosage levels of 5 MU, 15 MU, and 40 MU entrapped in the lipid vesicles. The Y-axis shows the individual's initials and the numbers above each bar are the fold increase over each individual's respective untreated skin sample.
Figure 2B:
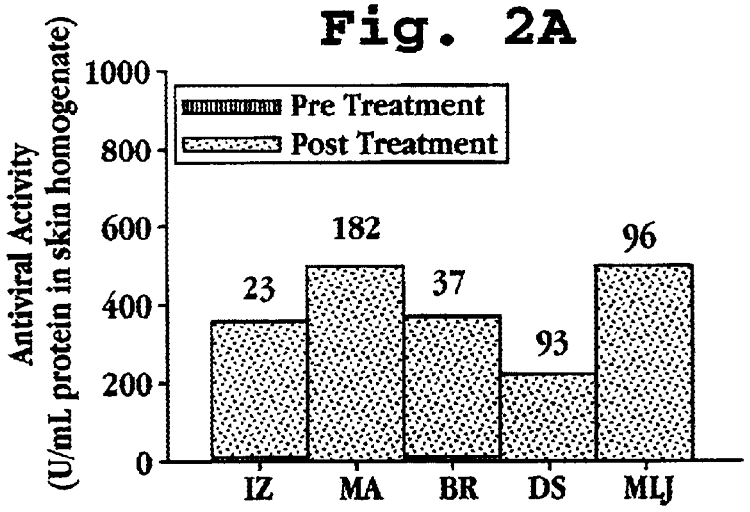
Figure 2C:
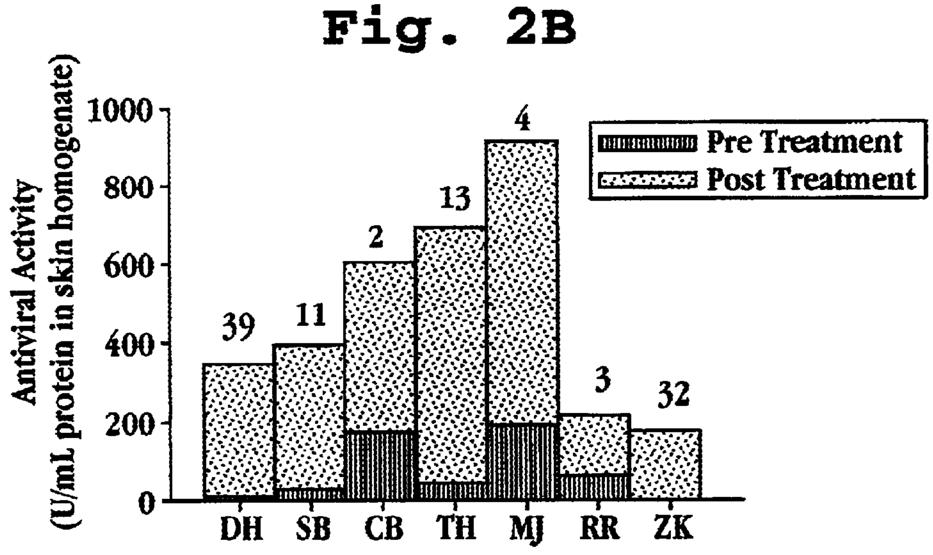

Skin biopsies analyzed by the antiviral assay for each subject are shown in FIGS. 2A–2C. The antiviral assay demonstrates delivery of IFN-α by the presence of antiviral bioactivity due to IFN-α or by possible induction of other antiviral compounds. Table 5 summarizes the average antiviral activity in skin homogenates for each of the three treatment groups.

TABLE 5

Antiviral activity in skin homogenates of subjects treated with IFNα in a biphasic delivery transdermal patch for 48 hours

| | Antiviral Activity[1] (U/mg protein in skin homogenate) mean ± SEM (range) Topical dose applied | | |
|---|---|---|---|
| Formulation | 5 million Units | 15 million Units | 40 million Units |
| INF-α Formulation | 120 ± 30 (n = 5) (15–200) | 380 ± 60 (n = 5) (200–500) | 400 ± 80 (n = 7) (160–930) |
| Control, placebo formulation | 7 ± 2 (n = 5) | 13 ± 5 (n = 5) | not determined |
| Untreated skin | not determined | not determined | 75 ± 30 (n = 7) |
| Statistics[2] | p < 0.05 | p < 0.005 | p < 0.01 |

[1]data are not corrected for loss of activity due to manufacturing and treatment.
[2]Statistical analysis by paired t-test.

The results in Table 5 from the antiviral assay indicate a dose dependent increase in antiviral activity. There was significant 5-fold average increase in delivery as the dose was increased from 5 to 15 MU. The expression of data per mg protein in skin homogenate accounts for skin biopsy thickness and recovery of tissue in the homogenization process.

Baseline levels of antiviral activity was determined in untreated volunteers (the 40 MU-dose group), as well as in volunteers treated with a placebo biphasic delivery system prior to treatment with the active formulations. Also as seen in Table 5, both untreated and placebo treated controls (baseline) showed relatively low levels of antiviral activity (overall range 7–75 U/mg protein in homogenate). The inter-individual variability of the baseline was taken into account in the calculation of fold increase in antiviral activity in the skin post-treatment vs. pre-treatment, since each individual served as his/her own control.

Figure 3A:
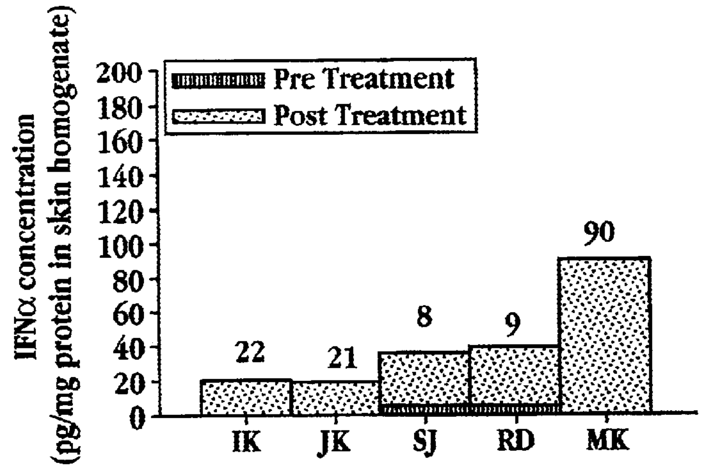
FIGS. 3A–3C are graphs showing IFN-α concentration as pg/mg protein in skin homogenate prepared from samples taken from human subjects after transdermal administration of IFN-α from biphasic lipid vesicles containing monolauroyl lysine and IFN-α at dosage levels of 5 MU, 15 MU, and 40 MU entrapped in the lipid vesicles. The Y-axis shows the individual's initials and the numbers above each bar are the fold increase over each individual's respective untreated skin sample.
Figure 3B:
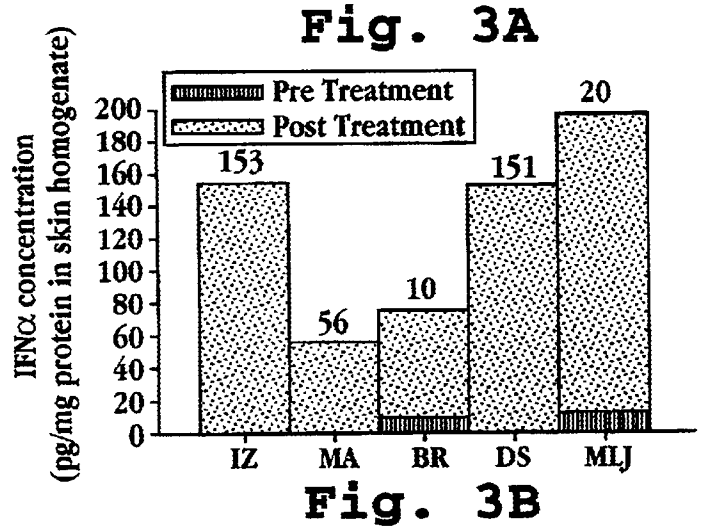
Figure 3C:
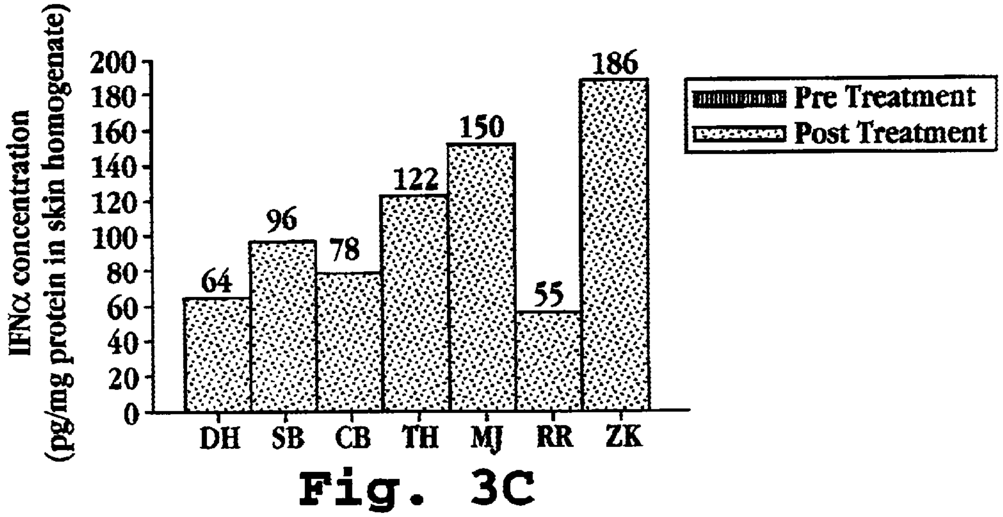

FIGS. 3A–3C show the IFN-α concentration in the skin homogenates for each individual in each of the three treatment groups. The ELISA assay demonstrates delivery of IFN-α by a sandwich immunoassay using an IFN-α-specific antibody and a horseradish peroxidase labelled secondary antibody for detection. The data show for each individual in FIGS. 3A–3C is averaged for each treatment group in Table 6.

antiviral assay (Table 5). Namely, there was a 3-fold increase in IFN-α levels in the post-treatment skin homogenates of subjects treated with a 15 MU dose of IFN-α compared to the subjects treated with a 5 MU dose of IFN-α. No significant further increase was observed as the dose was increased to 40 MU. Baseline IFN-α levels were very low or undetectable under the conditions used in this study, as can be seen from the placebo and untreated control values in the table.

4. Transdermal Drug Delivery: Analysis of Blood Samples

Figure 4A:
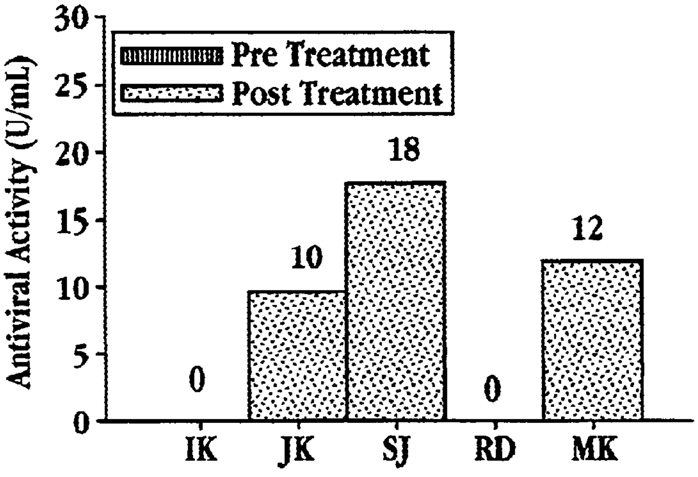
FIGS. 4A–4C are graphs showing the antiviral activity in serum samples taken from human subjects after transdermal administration of IFN-α from biphasic lipid vesicles containing monolauroyl lysine and IFN-α at dosage levels of 5 MU, 15 MU, and 40 MU entrapped in the lipid vesicles. The Y-axis shows the individual's initials and the numbers above each bar are the fold increase over each individual's respective untreated skin sample.
Figure 4B:
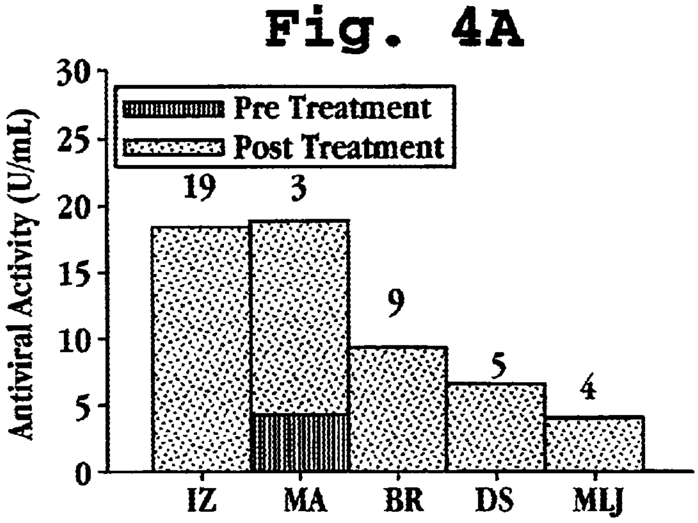
Figure 4C:
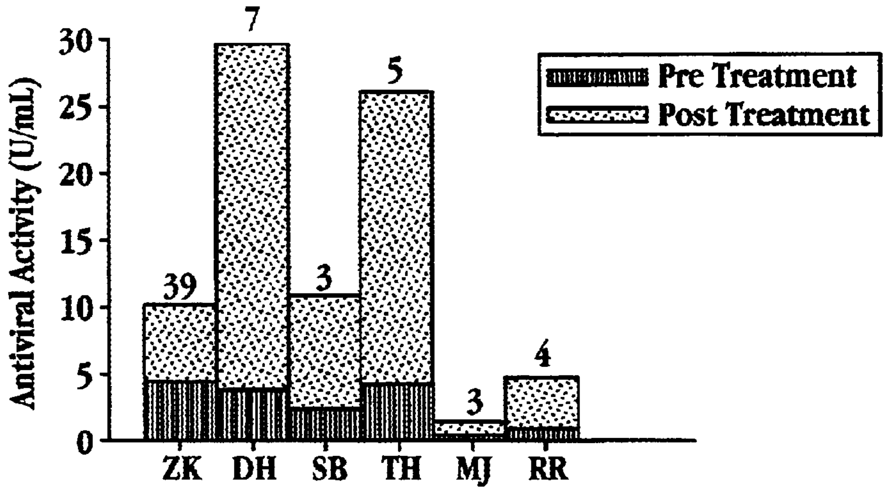

The blood samples collected from each subject before and after treatment with transdermal patch containing a biphasic lipid vesicle composition with entrapped IFN-α were analyzed by the antiviral assay to determine the amount of antiviral activity in the serum of each volunteer. The results for each subject are shown in FIGS. 4A–4C. The results show a significant increase in serum antiviral activity in the individual subjects in each treatment group.

Induction of 2-5A synthetase enzyme activity in peripheral blood mononuclear cells (PBMC) was used as an indication for the systemic delivery of IFN-α from biphasic delivery systems. The 2-5A synthetase enzyme activity for each individual in each treatment group is shown in FIGS.

TABLE 6

Amount of IFN-α detected by ELISA in skin homogenates of volunteers treated topically with IFN-α in a biphasic delivery system for 48 hours

| | Amount of IFN-α[1] (pg/mg protein in skin homogenate) mean ± SEM (range) Topical dose applied | | |
|---|---|---|---|
| Formulation | 5 million Units | 15 million Units | 40 million Units |
| INF-α Formulation | 40.1 ± 12.8 (n = 10) (20.6–90.1) | 122.4 ± 25.9 (n = 10) (55.5–186.0) | 107.5 ± 18.1 (n = 7) (55.2–186.3) |
| Control, placebo formulation | 1.6 ± 1.0 (n = 5) | 3.2 ± 2.0 (n = 5) | not determined |
| Untreated skin | not determined | not determined | not determined |
| Statistics[2] | p < 0.05 | p < 0.02 | p < 0.002 |

[1]data are not corrected for loss of activity due to manufacturing and treatment.
[2]Statistical analysis by paired t-test The data in Table 6 based on the ELISA assay shows a similar trend as observed for the data analyzed by the 5A–5C. The averaged data within each treatment group is summarized in Table 7.

TABLE 7

2–5A synthetase enzyme activity in PBMC cellular fraction of blood taken from subjects treated transdermally with IFN-α in a biphasic delivery system for 48 hours

| | 2–5A synthetase[1] (pmole 2–5A polyadenylate/mg protein/h) mean ± SEM (range) Topical dose applied | | |
|---|---|---|---|
| Formulations | 5 million Units | 15 million Units | 40 million Units |
| INF-α Formulation | 222.3 ± 41.8 (n = 5) (108.6–311.0) | 213.7 ± 42.5 (n = 5) (107.0–323.3) | 1639 ± 421 (n = 4) (232.9–2660) |
| Untreated skin control | 48.5 ± 18.3 (n = 5) | 110.7 ± 34.5 (n = 5) | 330.9 ± 182.9 (n = 4) |
| Placebo control | 35.4 ± 11.4 (n = 5) | 35.4 ± 11.4 (n = 5) | not done |
| Statistics[2] | p < 0.02 | p < 0.02 | p < 0.10 |

Figure 5A:
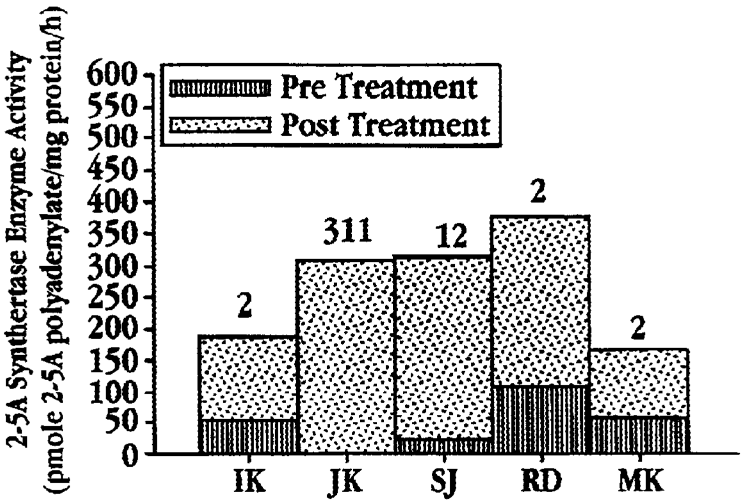
FIGS. 5A–5C are graphs showing the 2-5A synthetase enzyme activity in serum samples taken from human subjects after transdermal administration of IFN-α from biphasic lipid vesicles containing monolauroyl lysine and IFN-α at dosage levels of 5 MU, 15 MU, and 40 MU entrapped in the lipid vesicles. The Y-axis shows the individual's initials and the numbers above each bar are the fold increase over each individual's respective untreated skin sample.
Figure 5B:
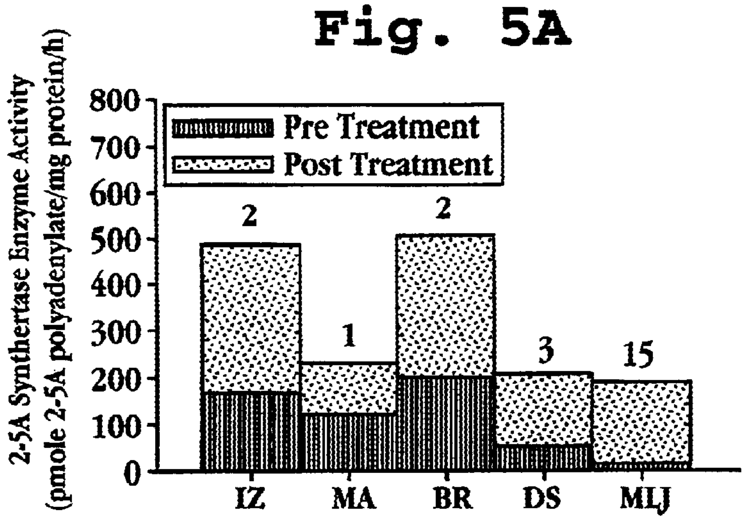
Figure 5C:
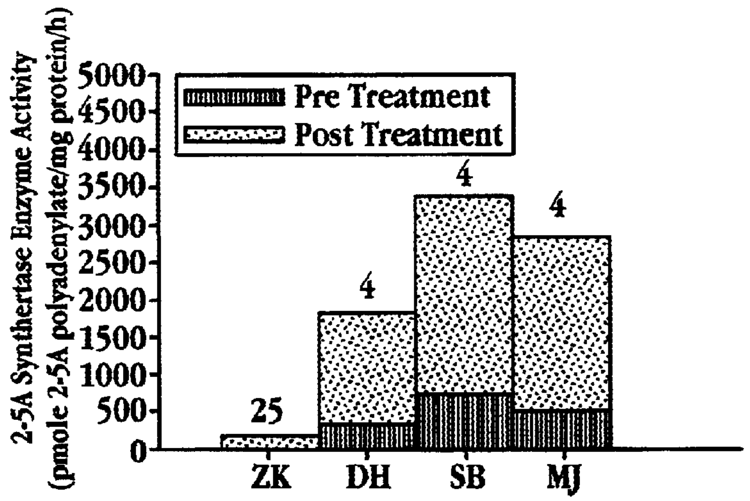

[1]data are not corrected for loss of activity due to manufacturing and treatment
[2]Statistical analysis by paired t-test Each individual served as his/her own control to account for inter-individual variability. As seen in the individual data shown in FIGS. 5A–5C, overall baseline levels varied from about 50–300 pmol/mg protein/h. There was a significant induction in enzyme activity in all three treatment groups compared to their untreated controls ($p<0.05$). There was no significant difference between the treatment groups receiving 5 MU IFN-α and 15 MU IFN-α, however, the difference between the groups treated with 15 MU IFN-α and 40 MU IFN-α was significant at $p<0.05$.

The skin biopsy taken from the site of application of the biphasic lipid vesicle-containing transdermal patch of each test subject was processed for immunohistochemistry. A skin sample from a representative individual in the treatment group receiving 40 MU IFN-α was compared visually to a skin section of control, untreated skin after staining both samples with anti-IFN-α antibodies. The photomicrographic images, while not shown here, show that the skin site treated with the biphasic delivery system has IFN-α specific immunostaining throughout the stratum corneum, epidermis and dermis. This staining pattern was characteristic in all volunteers in this treatment group.

Skin sections were also stained for Ki67 nuclear protein in proliferating cells using anti-M1B1 monoclonal antibodies (Rose et al., *J. Clin. Pathol.,* 47:1010 (1994)) and visualized. The photomicrographs of the skin sections are not shown here, but the anti-proliferative effect of IFN-α in the treated skin is evident from the decreased staining in the skin treated with IFN-α.

Table 8 shows the results of an anti-proliferation assay performed on skin sections of the test subjects in each treatment group after treatment with the respective dosages of IFN-α for 48 hours. The number of stained cells were counted before and after treatment sections. The decreased number of stained cells were expressed as a percentage.

TABLE 8

Anti-proliferation assay on skin sections of human volunteers after topical IFN-α treatment

| Dose (MU) | Average % decrease of proliferative cells stained by anti-Ki67 antibody[c] | anti-proliferative ratio[c] | p Value[d] |
|---|---|---|---|
| 5[a] | 14 | 1.21 | n.s. |
| 15[a] | 10 | 1.32 | n.s. |
| 40[b] | 38 | 2 | <0.1 |

[a]compared to placebo treated skin
[b]compared to untreated skin
[c]average number of proliferating cells in untreated skin (or placebo treated)/ average number of proliferating cells after treatment
[d]statistical analysis by paired t-test The in vivo results from the human subjects indicate that the biphasic lipid vesicle composition of the invention when administered transdermally is effective to deliver therapeutically significant amounts of IFN-α to the skin and the blood.

IV. METHODS OF TREATMENT

In another aspect, the invention includes a method for administering an interferon to a subject. In the method, a dosage form comprising the biphasic lipid vesicle composition described above is administered to a subject having a condition responsive to treatment with an interferon. The dosage form is one suitable to achieve dermal or transdermal administration of the biphasic lipid vesicle composition. As discussed above, dermal or transdermal delivery can be achieved according to selection of the acylated amino acid used in the lipid vesicle formulation.

In one embodiment, the dosage form is a simple topical cream, ointment, gel or the like comprised of the biphasic lipid vesicle composition. Preparation of topical dosage forms is well known to those of skill in the art.

In another embodiment, the dosage form is a transdermal delivery system, or transdermal patch. The reservoir of the patch contains the biphasic lipid vesicle composition in accord with the invention.

Interferons are recognized as clinically valuable compounds for the treatment of a variety of conditions, including use as anti-viral agents, for example, in the treatment of AIDS (Lane, H. C., *Semin. Oncol.* 18:46–52 (October 1991)), viral hepatitis including chronic hepatitis B and hepatitis C (Woo, M. H. and Burnakis, T. G., Ann. Pharmacother. 31:330–337 (March 1997); Gibas, A. L., *Gastroenterologist* 1:129–142 (June 1993)), papilloma viruses (Levine, L. A. et al., *Urology,* 47:553–557 (April 1996)), herpes (Ho, M., *Annu. Rev. Med.* 38:51–59 (1987)), cytomegalovirus (CMV) (Yamamoto, N. et al., *Arch. Virol.* 94:323–329 (1987)), viral encephalitis (Wintergerst et al., *Infection* 20:207–212 (July 1992)), and in the prophylaxis of rhinitis (Ho, M., *Annu. Rev. Med.* 38:51–59 (1987)).

Interferons also find use as anti-parasitic agents, where interferons have been suggested for anti-parasite therapy, for example, IFN-gamma for treating *Cryptosporidium parvum* infection (Rehg, J. E., *J. Infect. Diseases,.* 174:229–232 (July 1996)). As anti-bacterial agents, IFN-gamma has been used in the treatment of multidrug-resistant pulmonary tuberculosis (Condos et al., *Lancet* 349:1513–1515 (1997)), and as anti-cancer agents, interferon therapy has been used in the treatment of numerous cancers (e.g., hairy cell leukemia (Hofmann et al., *Cancer Treat.* Rev. 12 (Suppl. B):33–37 (December 1985)), acute myeloid leukemia (Stone et al., *Am. J. Clin. Oncol.,* 16:159–163 (April 1993)), osteosarcoma (Strander et al., *Acta Oncol.* 34:877–880 (1995)), basal cell carcinoma (Dogan et al., *Cancer Lett.* 91:215–219 (May 1995)), glioma (Fetell et al., *Cancer* 65:78–83 (January 1990)), renal cell carcinoma (Aso et al., *Prog. Clin. Biol. Res.,* 303:653–659 (1989)), multiple myeloma (Peest et al., *Br. J. Haematol.,* 94:425–432 (September 1996)), melanoma (Ikic et al., *Int. J. Dermatol.* 34:872–874 (December 1995)), and Hodgkin's disease (Rybak et al., *J. Biol. Response Mod.* 9:1–4 (February 1990)). Synergistic treatment of advanced cancer with a combination of alpha interferon and temozolomide has also been reported (WO 97/12630). In immunotherapy, interferons have been used clinically for immunosuppression, for example, to prevent graft vs. host rejection, or to curtail the progression of autoimmune diseases, such as arthritis, multiple sclerosis, or diabetes. IFN-beta is approved for sale in the United States for the treatment of multiple sclerosis (i.e., as an immunosuppressant). In addition, immunotherapy with recombinant IFN-alpha (in combination with recombinant human IL-2) has been used successfully in lymphoma patients following autologous bone marrow or blood stem cell transplantation, and may intensify remission following transplantation (Nagler et al., *Blood* 89:3951–3959 (June 1997)). The administration of IFN-gamma has been used in the treatment of allergies in mammals (WO 87/01288). It has also recently been demonstrated that there is a reduced production of IL-12 and IL-12-dependent IFN-gamma release in patients with allergic asthma (van der Pouw Kraan et al., *J. Immunol.* 158:5560–5565 (1997)). Thus, interferon may be useful in the treatment of allergy by inhibiting the humoral response. Further, interferons may be used as an adjuvant or co-adjuvant to enhance or stimulate the immune response in cases of prophylactic or therapeutic vaccination (Heath, A. W. and Playfair, J. H. L., *Vaccine* 10:427–434 (1992)).

In a preferred embodiment of the invention, the biphasic lipid vesicle composition of the invention is intended for treatment of human papilloma virus by topical application of a dosage form containing the biphasic lipid vesicles having entrapped IFN-α.

In another aspect, the invention includes a method for treating human papilloma virus (HPV). In the method, biphasic lipid vesicles comprising IFN-α and an acylated amino acid are prepared as described above. The lipid vesicles are contacted with the skin of a person in need of treatment. More than 60 different human papilloma viruses have been identified; for example, type 2 causes warts on the hands, type 6 is associated with genital warts, and type 13 causes flat, wartlike lesions in the mouth. Types 16 and 18 are possibly linked with cancers.

Genital warts, also called condylomata acuminata or venereal warts, are spread by sexual contact with an infected person. It is estimated that as many as one million new cases of genital warts are diagnosed in the United States each year. HPV has been shown to be associated with cervical dysplasia, which possibly develops into cervical cancer in women. Cervical cancer is the second most common cancer in women worldwide and nearly all women with cervical cancer test positive for HPV.

Early and effective treatment of persons infected with HPV is desired. In accord with the present invention, a person presenting symptoms of infection with HPV, such as genital warts, is treated with the lipid vesicle composition by direct application of the lipid vesicles, in a suitable vehicle if desired, to the site of infection, e.g., the genital warts.

V. EXAMPLES

The following examples further illustrate the invention described herein and are in no way intended to limit the scope of the invention.

Materials

IFN-$\alpha_{2b}$ (Intron A) was obtained from Schering-Plough. Synthetic beeswax was obtained from Croda, Toronto, Ontario. DOWICIL was obtained from Dow Chemical (Midland, Mich.). Phospholipid EFA™ was purchased from PEBRO (Missassauga, Ontario, Canada). Canola oil was obtained from Natural Oils International, Arleta Calif.

Methods

1. Antiviral Assay

Antiviral activities in skin homogenates were determined in triplicates of serial dilutions using Madin-Darby bovine kidney (MDBK) cells and vesicular somatitis virus (VSV) in 96-well microtiter plates. Activity (U) in the samples was calculated based on serial dilutions of an IFN-α standard.

The MDBK cells were grown to confluency in 150 $cm^2$ tissue culture flasks in supplemented MEM in a 37° C., 5% $CO_2$ incubator. The monolayers in each flask were infected with VSV (2.5×$10^5$ plaque forming unit (PFU)) in 3 mL supplemented minimal essential medium (MEM) for MDBK; 5×$10^5$ PFU in 5 mL supplemented MEM for WISH). The infected flasks were incubated for 60 min at 37° C. and were shaken every 15 min. The medium was poured out and 20 mL supplemented MEM was added to each infected flask and then incubated overnight at 37° C. When the cells were around 20% confluent, the infected flasks were frozen at −70° C. To release the VSV from the cells, the medium was thawed at room temperature. The supernatants were transferred to a 50 mL centrifuge tube and centrifuged at 500 rpm for 10 minutes. The virus-rich supernatants were pooled and placed on ice. The virus stock was aliquot into 500 L/vial and stored at −70° C. These VSV stocks were used for the antiviral assay. A single cell suspension of MDBK cells was prepared from a confluent culture and the MDBK cells were resuspended at 6–7×$10^5$ cells/mL in supplemented MEM. 50 μL of supplemented MEM was added to each well of a 96-well flat-bottomed microtiter plate. 50 μL of IFN standard was added to well 3 of row A and B. 50 μL of the first sample was added to well 3 of row C and D, and repeated for samples 2 and 3. A 2-fold serial dilution of IFN samples was prepared by gently mixing the contents of well 3 and then transferring 50 μL from well 3 to well 4, then from 4 to well 5, etc., through well 12. 50 μL of sample was discarded from well 12. At this point, each well contained 50 μL. 50 μL cells were added to each well and the plate was agitated to ensure the cells were evenly distributed. The plate was incubated overnight at 37° C. The VSV was diluted with supplemented MEM to 10000 PFU/mL. The supernatants were aspirated from each well of the microtiter plate with an 8-channel pipettor. Each well in vertical row 1 had 100 mL supplemented MEM added. 100 mL virus was added to each well, starting with row 2 (1000 PFU/well). The plate was incubated 20–24 hours at 37° C. The monolayers were examined, prior to washing and fixing the cells, using an inverted microscope. In the cell control wells, uniform monolayers were observed. In the virus control wells, the monolayers were completely destroyed. The supernatants were removed from each well. Each well was washed three times with 100 mL cold HBSS. The final wash was aspirated and replaced with 100 mL of 5% formalin in each well and incubated 10 minutes at room temperature. The formalin was shaken from the plate into a sink with the water running. 100 μL of 0.05% Crystal Violet in 20% ethanol was added to each well and incubated for 10 minutes at room temperature. The plate was rinsed with tap water, inverted on absorbent paper and allowed to dry. The samples were read spectrophotometrically, by adding 100 μL of 100% methanol to each well of the plate. The plate was agitated to elute the dye from the fixed cells. The absorbance was read at 595 nm.

Standards used in the bioassay: IFN-α 100 U/mL or 800 U/mL. Interferon-α standard diluted in serum (800 U/mL or 100 U/mL).

2. ELISA Assay

To determine IFN-α concentration in skin homogenates, Cytoscreen™ ELISA kit (Medicorp, Montreal, PQ) was used. The sensitivity of the assay is <25 pg/mL and the range of concentration is 0–500 pg/mL. The assay is specific for human IFN-α with no cross-reactivity with human IFNβ, IFNγ or IFNω. The results are expressed as pg IFN-α/mg skin.

3. 2-5A Synthetase Assay 2-5A synthetase was determined by a $^{125}$I-2-5A radioimmuno assay kit (Eiken Chemical Corp., Tokyo, Japan) using rabbit anti-human 2-5A antibody and goat antirabbit IgG as secondary antibody. Briefly, 2-5A synthetase was extracted from the samples by poly (I) poly (C) agarose for 10 min. After the addition of ATP solution (24 μg/mL) and incubation, 100 μL $^{125}$I-2-5A was added, followed by the primary and secondary antibody. Radioactivity bound was determined by gamma counting. 2-5A synthetase is measured as pmol 2-5A produced/100 mL/h and subsequently expressed as nmole enzyme/mg protein 1 h in skin homogenate. All samples were run in duplicates.

4. Immunohistochemistry

To demonstrate IFNα-specific immunostaining, paraformaldehyde fixed tissues were processed for parafilm embedding. Sections 5 μm in thickness were cut and after antigen retrieval with 10 mM Na-citrate the sections were incubated with mouse anti-human interferon alpha antibody (1:2,000–1:5,000), which were in turn treated with a biotinylated rabbit anti-mouse secondary antibody and stained by the Avidin Biotin Complex (ABC) method.

To demonstrate the anti-proliferative effect of IFNα, paraformaldehyde fixed skin sections were selectively stained for Ki67 nuclear protein in proliferating cells using anti-M1B1 monoclonal antibodies, according to Rose et al. *J. Clin. Pathol.,* 47:1010 (1994).

Example 1

Synthesis of N-Eicosanoyl-L-serine (PDM-3)

A. Preparation of Eicosanoic Acid N-hydroxysuccinimide Ester Intermediate

Eicosanoic acid (5.0 mmol) was dissolved in 40 mL of dichloromethane and 10 mL of N,N-dimethylformamide. 1-N-Hydroxysuccinimide (5.0 mmol) and N,N-dicyclohexyl-carbodiimide (5.0 mmol 10.0 mL, of 0.5 M solution) was added at −5° C. and the solution allowed to warm up to room temperature and the reaction mixture stirred at room temperature for 16 hr. Dicyclohexyl urea precipitate was filtered off. The filtrate was concentrated and the N-hydroxysuccinimide ester derivative purified by crystallization from dichloromethane-n-hexane solution.

B. Preparation of N-Eicosanoyl-L-serine

Asolution of L-serine (1.2 mmol) and sodium bicarbonate (1.2 mmol) in water, 2 mL was added to N-hydroxysuccinimidyl eicosanoate dissolved in p-dioxane:tetrahydrofuran (1:1), 20 mL, and stirred at room temperature for 10 hr. The reaction mixture was treated with water for 1 hr to hydrolyze the unreacted N-hydroxysuccinimide ester. The organic phase was evaporated on a rotary evaporator under vacuum, The residual aqueous phase was cooled in an ice bath and acidified with concentrated hydrochloric acid to pH 3.0. The product was filtered off and crystallized from dichloromethane-ethyl acetate solution.

Example 2

Synthesis of N-Eicosanoyl-L-threonine (PDM-4)

A solution of L-threonine (1.2 mmol) and sodium bicarbonate (1.2 mmol) in water, 2 mL was added to N-hydroxysuccinimidyl eicosanoate dissolved in p-dioxane:tetrahydrofuran (1:1), 20 mL, and stirred at room temperature for 10 hr. The reaction mixture was treated with water for 1 hr to hydrolyze the unreacted N-hydroxysuccinimide ester. The organic phase was evaporated on a rotary evaporator under vacuum, The residual aqueous phase was cooled in an ice bath and acidified with concentrated hydrochloric acid to pH 3.0. The product was filtered off and crystallized from dichloromethane-ethyl acetate solution.

Example 3

In vitro Adminstration of IFN-α

Materials

IFN-$\alpha_{2b}$ (Intron A) was obtained from Schering-Plough. Synthetic beeswax was obtained from Croda, Toronto, Ontario. DOWICIL was obtained from Dow Chemical (Midland, Mich.). Phospholipid EFA™ was purchased from PEBRO (Missassauga, Ontario, Canada). Canola oil was obtained from Natural Oils International, Arleta Calif.

A. Biphasic Lipid Vesicle Preparation

An anhydrous lipid gel was prepared by mixing the following components together:

| Component | Amount (% w/w) |
|---|---|
| Phosphatidylcholine[1] | 5 |
| Cholesterol | 2 |
| Acylated amino acid[2] | 2 |
| Stearic acid | 1 |
| Propylene glycol | 7 |

[1]Phospholipon ®90H, Rhone Poulenc Rorer Anerican Lecithin Company, Dunbury CT

[2]see specific studies for the acylated amino acid added

The lipids and the solvents were weighted into a glass container and warmed to 65–75° C. by intermittent heating, and gently mixed.

An oil-in-water emulsion was prepared by combining the hydrophilic ingredients in a container and combining the lipophilic ingredients in another container:

| | Amount (% w/w) |
|---|---|
| Hydrophilic Ingredients | |
| distilled water | q.s. to 100 |
| PEFA[1] | 4.0 |
| Methylparaben | 0.15 |
| Propylparaben | 0.05 |
| DOWICIL[2] | 0.05 |
| Lipophilic Ingredients | |
| canola oil | 4.0 |
| glyceryl monostearate | 1.0 |
| cetyl alcohol | 0.6 |
| synthetic beeswax | 0.28 |

[1]PEFA = linoleamidopropyl propylene glycol-dimonium chloride

[2]Dowicil = 1-(3-chlorallyl)-3,4,7-triaza-1-azoniaadamantane chloride

The oil-in-water emulsion was prepared by adding the lipophilic mixture to the hydrophilic ingredient mixture at 60–80° C. in a homogenizer at 20–80 psig for 5–30 minutes to obtain a small droplet size of less than about 0.5 μm.

Biphasic lipid vesicles were prepared by simultaneously adding the oil-in-water emulsion and an aqueous solution containing 5 million units of IFN-α to the lipid gel, which was warmed to 55° C. The gel, IFN-α and emulsion were vigorously mixed by vortexing or propeller mixing to achieve the desired particle size.

B. Diffusion Cell Studies

The diffusion of IFN-α into human skin was investigated using flow-through diffusion cells. Full thickness human skin (thickness approx. 2.0 mm) obtained from plastic surgery and kept at −20° C. was placed in the flow through diffusion cells. The diffusion cells are designed such that fluid may be continuously pumped through them in order to maintain sink conditions (flow rate: 3 mL/hour). A phosphate buffer (PBS: 7.5 mM $Na_2HPO_4$, 2.5 mM $NaH_2PO_4$, 141.2 mM NaCl) isotonic with body fluids was used and the temperature was maintained at 32° C. by a circulating water bath.

About 100 mg of formulation was applied on the stratum corneum side of the skin to 4 diffusion cells (n=4). Each experiment was conducted for a period of 24 hours continuously. After 24 hours, the skin was removed from the diffusion cell and the surface was washed with sterile distilled water (3×10 mL). Using an adhesive tape the residual formulation from the surface of the skin that was not removed in the washing process was stripped (1×).

The amount of IFN-α that penetrated into the skin was assessed using a bioassay described above in the Methods section that measures interferon antiviral activity. A skin homogenate was prepared using the skins. IFN-α present in the homogenate was extracted by centrifugation with 2 mL of PBS. The accuracy of the antiviral activity bioassay was verified by spiking 100 U/ml IFN-α on an untreated skin homogenate supernatant and extracting the IFN-α via centrifugation. The supernatant was either PBS or PBS containing 0.005% of Tween 80. To check the possibility of interference from background IFN (interferon already present in the skin homogenate) the supernatant from skin homogenate where no interferon was added was also analyzed. The results are shown in Table 3.

Example 4

In vivo Administration of IFN-α to Guinea Pigs

Guinea pigs (n=3/group) were shaved with an electric razor 24 hours prior to the application of a skin patch containing a test formulation. The skin was lightly washed with distilled water and patted dry with tissue prior to the addition of the patch. The patch was applied by removing the backing paper from the adhesive foam and firmly pressing the patch to a clean area of skin away from any skin abrasion and located in a position that the animal is unlikely to access. The patch was covered with OPSITE™ occlusive dressing and a plastic tape to keep the patch in place for 24 hours. The patching was carried out under anesthesia with halothane. After treatment the patch was removed under anesthesia. Any remaining formulation was collected for analysis and the skin was checked for general condition.

After patch removal, the skin surface was cleaned by wiping the area once with a dry tissue, 4×with a tissue soaked in 70% ethanol, 4 swabs with 0.5% (v/v) Tween 80 in distilled water using a cotton wool swab, finally 4×with a tissue soaked in 70% ethanol. The section of the skin marked as treatment area was removed using clean sharp scissors, ensuring that only the treated area was sampled. The skin samples were frozen until analysis.

The animals were killed by cardiac puncture. Blood was collected into vacutainer tubes and centrifuged immediately. Serum was collected and aliquots were stored at −80° C. until used.

The frozen skin samples were weighed and pulverized in liquid $N_2$ by five blows from a hammer in a tissue pulveriser (preincubated in liquid $N_2$). The pulverized tissue was reweighed to calculate the recovery of material and extracted by moderate vortexing with 5–10 volumes of PBS containing 1 mg/mL leupeptin and 20 mg/mL soybean trypsin inhibitor as protease inhibitors. The skin was resuspended in buffer and then sonicated 3×15 seconds, with 1 min intervals on ice, then centrifuged at 500 g for 10 min at 4° C. to remove undisrupted cells and connective tissue. The resulting supernatants were termed "whole cell homogenates" and were used immediately or aliquoted into 2–300 mL aliquots and stored at −80° C. Skin homogenates were used to determine IFN-α absorption by antiviral assay described above in the Methods section. Results are shown in FIGS. 1A–1B.

Example 5

In vivo Administration of IFN-α to Humans

A. Biphasic Lipid Vesicle Preparation

An anhydrous lipid gel was prepared by mixing the following components together:

| Component | Amount (% w/w) |
|---|---|
| Phosphatidylcholine[1] | 10 |
| Cholesterol | 2 |
| monolauroyl lysine[2] | 2 |
| Propylene glycol | 7 |

[1]Phospholipon ®90H, Rhone Poulenc Rorer American Lecithin Company, Dunbury CT
[2]see Table 1A for the chemical name and structure The lipids and the solvents were weighed into a glass container and warmed to 65–75° C. by intermittent heating, and gently mixed.

An oil-in-water emulsion was prepared by combining the following hydrophilic ingredients in a container and combining the following lipophilic ingredients in another container:

| | Amount (% w/w) |
|---|---|
| Hydrophilic Ingredients | |
| distilled water | q.s. to 100 |
| PEFA[1] | 4.0 |
| Methylparaben | 0.15 |
| Propylparaben | 0.05 |
| DOWICIL[2] | 0.05 |
| Cetyl alcohol | 0.6 |
| Lipophilic Ingredients | |
| Canola oil | 4.0 |
| Glyceryl monostearate | 1.0 |
| Synthetic beeswax | 0.28 |

[1]PEFA = linoleamidopropyl propylene glycol-dimonium chloride
[2]Dowicil = 1-(3-chlorallyl)-3,4,7-triaza-1-azoniaadamantane chloride The oil-in-water emulsion was prepared by adding the lipophilic mixture to the hydrophilic ingredient mixture at 60–80° C. in a homogenizer at 20–80 psig for 5–30 minutes to obtain a small droplet size of less than about 0.5 μm.

In separate containers, aqueous solutions of IFN-α were prepared having activities of 5 MU, 15 MU and 40 MU. Lyophilized IFN-α (Intron A) was dissolved in part of the formulation water to the total quantity required for the batch size.

Biphasic lipid vesicles were prepared by simultaneously adding the oil-in-water emulsion and an IFN-α aqueous solution at a selected concentration to the lipid gel, which was warmed to 55° C. The lipid gel, IFN-α solution, and emulsion were vigorously mixed by vortexing or propeller mixing to achieve the desired particle size.

B. Transdermal Patch

The biphasic lipid vesicle preparations were placed in transdermal devices constructed from a backing member peripherally joined to a styrofoam adhesive member. The patches had a 5 cm outer diameter and a 3 cm inner diameter to give an active delivery area of about 7 $cm^2$. One gram of formulation was loaded into each patch.

C. In vivo Administration to Humans

1. Phase I

Seventeen human volunteers were randomized into three treatment groups. In Phase I of the study, all volunteers in each group were treated with a placebo transdermal patch containing biphasic lipid vesicles of the composition described above with no IFN-α. The patches were adhesively applied to the inner upper arm and covered with OPSITE transparent adhesive for added protection. After the 48 hour test period, 6 mm punch biopsies and blood samples were collected from each subject for analysis.

Skin sites for biopsies were prepared by removing any residual cream by thorough wiping with tissue paper and swabbing with 70% alcohol followed by local anesthesia with 1% lidocaine-epinephrine solution.

Biopsy samples were used for immunohistochemistry and for homogenate preparation for antiviral, ELISA and 2-5 A synthetase assays, and procedures for each are provided above in the Methods section. Blood samples were used to prepare serum for the antiviral and ELISA assays, and to extract peripheral blood mononuclear cells (PBMC) for the 2-5 A synthetase assay. Results are shown in FIGS. 2A–2C, 3A–3C and Tables 5 and 6.

2. Phase II

The human volunteers randomized during Phase I of the study were each treatment with a transdermal patch containing a biphasic delivery system of IFN-α, 5, 15 or 40 MU/g dose, for 48 hours. The patch was applied to the upper inner arm as described above. After the 48 hour test period, 6 mm punch biopsies and blood samples were collected as described above from each subject for analysis. In the test group treated with patches containing 40 MU/g skin biopsies were collected from untreated skin sites for analysis. Results are shown in FIGS. 4A–4C and 5A–5C and Tables 7 and 8.

Although the invention has been described with respect to particular embodiments, it will be apparent to those skilled in the art that various changes and modifications can be made without departing from the invention.

It is claimed:

1. An interferon-α composition, comprising biphasic lipid vesicles comprised of (i) a lipid bilayer comprising a phospholipid and a fatty acylated amino acid; (ii) an oil-in-water emulsion entrapped in the biphasic lipid vesicles, said oil-in-water emulsion being stabilized by a surfactant; and (iii) interferon-α entrapped in said vesicles;

said fatty acylated amino acid being represented by the formula:

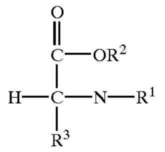

wherein $R^1$ is an acyl group having from 1–20 carbons, $R^2$ is hydrogen or an alkyl group, and $R^3$ corresponds to a modified or unmodified R group of an amino acid selected from the group consisting of glycine, alanine, serine, aspartic acid, arginine, valine, threonine, glutamic acid, leucine, cysteine, histidine, lsoleucine, tyrosine, asparagine, methionine, proline, tryptophan, phenylalanine, and glutamine;

wherein said composition when applied to the skin of a subject being effective to administer a therapeutically effective amount of interferon-α.

2. The composition of claim 1, wherein said acylated amino acid is for dermal administration of interferon-α.

3. The composition of claim 1, wherein said acylated amino acid is for transdermal administration of interferon-α.

4. The composition of claim 1, wherein said R group of amino acid is the R group of serine or threonine.

5. The composition of claim 1, wherein said oil-in-water emulsion further comprises a fatty alcohol.

6. The composition of claim 5, wherein said fatty alcohol is has between about 8–24 carbon atoms.

7. The composition of claim 1, wherein said oil-in-water emulsion further comprises a triglyceride.

8. The composition of claim 7, wherein said triglyceride is a pharmaceutically acceptable oil.

9. The composition of claim 8, wherein said synthetic oil is selected from the group consisting of canola oil and olive oil.

10. The composition of claim 1, wherein said oil-in-water emulsion is further comprised of a fatty glyceride dispersed in the water phase and stabilized by said surfactant.

11. The composition of claim 10, wherein said fatty glyceride is glycerol monostearate.

12. The composition of claim 1, wherein said lipid bilayer is further comprised of a sterol.

13. An interferon-α composition, comprising biphasic lipid vesicles comprised of (i) a lipid bilayer comprised of a phospholipid and an acylated amino acid represented by the formula:

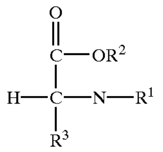

wherein $R^1$ is an acyl group having from 1–20 carbons, $R^2$ is hydrogen or an alkyl group, and $R^3$ corresponds to a modified or unmodified R group of an amino acid selected from the group consisting of glycine, alanine, serine, aspartic acid, arginine, valine, threonine, glutamic acid, leucine, cysteine, histidine, isoleucine, tyrosine, asparagine, methionine, proline, tryptophan, phenylalanine, and glutamine; (ii) an oil-in-water emulsion entrapped in the biphasic lipid vesicles, said oil-in-water emulsion comprised of a triglyceride that is dispersed in a water phase containing a fatty alcohol and that is stabilized by a surfactant; and (iii) interferon-α entrapped in said vesicles;

wherein said composition when applied to the skin of a subject being effective to administer a therapeutically effective amount of interferon-α.

14. The composition of claim 13, wherein said acylated amino acid is for dermal administration of interferon-α.

15. The composition of claim 13, wherein said acylated amino acid is for transdermal administration of interferon-α.

16. The composition of claim 13, wherein said R group of an amino acid is the R group of serine or threonine.

17. The composition of claim 13, wherein said lipid bilayer further includes cholesterol.

18. The composition of claim 13, wherein said triglyceride is canola oil.

19. The composition of claim 13, wherein said surfactant is a cationic phospholipid.

20. The composition of claim 13, wherein said lipid bilayer further includes cholesterol.

21. The composition of claim 13, wherein said triglyceride is a pharmaceutically acceptable oil.

22. The composition of claim 21, wherein said oil is selected from the group consisting of canola oil and olive oil.

23. The composition of claim 13, wherein fatty alcohol has between about 2–24 carbon atoms.

24. An interferon-α composition, comprising biphasic lipid vesicles comprised of (i) a lipid bilayer comprising a phospholipid and a fatty acylated amino acid; (ii) an oil-in-water emulsion entrapped in the biphasic lipid vesicles, said oil-in-water emulsion being stabilized by a surfactant; and (iii) interferon-α entrapped in said vesicles;

said fatty acylated amino acid being represented by the formula:

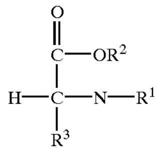

wherein $R^1$ is hydrogen or an acyl group having less than 16 carbons and $R^2$ is hydrogen or an alkyl group, but when $R^1$ is hydrogen, $R^2$ is an alkyl group, and $R^3$ corresponds to a modified or unmodified lysine R group;

wherein said composition when applied to a subject being effective to administer a therapeutically effective amount of interferon-α.

25. The composition of claim 24, wherein said acylated amino acid is for dermal administration of interferon-α.

26. The composition of claim 24, wherein said acylated amino acid is for transdermal administration of interferon-α.

27. The composition of claim 24, wherein said oil-in-water emulsion further comprises a fatty alcohol.

28. The composition of claim 27, wherein said fatty alcohol is has between about 8–24 carbon atoms.

29. The composition of claim 24, wherein said oil-in-water emulsion further comprises a triglyceride.

30. The composition of claim 29, wherein said triglyceride is a pharmaceutically acceptable oil.

31. The composition of claim 30, wherein said oil is selected from the group consisting of canola oil and olive oil.

32. The composition of claim 24, wherein said oil-in-water emulsion is further comprised of a fatty glyceride dispersed in the water phase and stabilized by said surfactant.

33. The composition of claim 32, wherein said fatty glyceride is glycerol monostearate.

34. The composition of claim 24, wherein said lipid bilayer is further comprised of a sterol.

35. An interferon-α composition, comprising biphasic lipid vesicles comprised of (i) a lipid bilayer comprised of a phospholipid and an acylated amino acid represented by the formula:

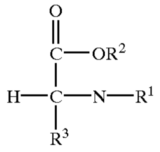

wherein $R^1$ is hydrogen or an acyl group having less than 16 carbons and $R^2$ is hydrogen or an alkyl group, but when $R^1$ is hydrogen, $R^2$ is an alkyl group, and $R^3$ corresponds to a modified or unmodified lysine R group; (ii) an oil-in-water emulsion entrapped in the biphasic lipid vesicles, said oil-in-water emulsion comprised of a triglyceride that is dispersed in a water phase containing a fatty alcohol and that is stabilized by a surfactant; and (iii) interferon-α entrapped in said vesicles;

wherein said composition when applied to a subject being effective to administer a therapeutically effective amount of interferon-α.

36. The composition of claim 35, wherein said acylated amino acid is for dermal administration of interferon-α.

37. The composition of claim 35, wherein said acylated amino acid is for transdermal administration of interferon-α.

38. The composition of claim 35, wherein said lipid bilayer further includes cholesterol.

39. The composition of claim 35, wherein said triglyceride is canola oil.

40. The composition of claim 35, wherein said surfactant is a cationic phospholipid.

41. The composition of claim 35, wherein said lipid bilayer further includes cholesterol.

42. The composition of claim 35, wherein said triglyceride is a pharmaceutically acceptable oil.

43. The composition of claim 35, wherein said oil is selected from the group consisting of canola oil and olive oil.

44. The composition of claim 35, wherein fatty alcohol has between about 2–24 carbon atoms.

45. The composition of claim 4, wherein said acylated amino acid is selected from the group consisting of N-capryloyl-L-threonine methyl ester, N-eicosanoyl-L-serine, and N-eicosanoyl threonine.

46. The composition of claim 16, wherein said acylated amino acid is selected from the group consisting of N-capryloyl-L-threonine methyl ester, N-eicosanoyl-L-serine, and N-eicosanoyl threonine.

* * * * *